United States Patent [19]

Paget et al.

[11] 4,118,742

[45] Oct. 3, 1978

[54] CARBONYL-SUBSTITUTED 1-SULFONYLBENZIMIDAZOLES

[75] Inventors: Charles J. Paget; James W. Chamberlin, both of Indianapolis; James H. Wikel, Greenwood, all of Ind.

[73] Assignee: Eli Lilly and Company, Indianapolis, Ind.

[21] Appl. No.: 750,991

[22] Filed: Dec. 15, 1976

Related U.S. Application Data

[63] Continuation-in-part of Ser. No. 608,415, Aug. 28, 1975, abandoned.

[51] Int. Cl.² .......................................... C07D 235/30

[52] U.S. Cl. .................................. 548/306; 260/293.6; 260/306.8 R; 260/306.8 D; 260/307 A; 260/307 G; 260/308 R; 260/308 A; 542/416; 544/132; 544/137; 544/138; 544/139

[58] Field of Search .................... 260/309.2, 247.1 L, 260/293.6; 548/306; 544/139

[56] References Cited

U.S. PATENT DOCUMENTS

| | | | |
|---|---|---|---|
| 3,682,952 | 8/1972 | Actor et al. | 260/309.2 |
| 3,721,678 | 3/1973 | Burton et al. | 260/309.2 |
| 3,850,954 | 11/1974 | Widdig et al. | 260/309.2 |
| 3,853,908 | 12/1974 | Widdig et al. | 260/309.2 |

*Primary Examiner*—Natalie Trousof
*Attorney, Agent, or Firm*—Kathleen R. S. Page; Arthur R. Whale

[57] ABSTRACT

Certain carbonyl-substituted-1-sulfonylbenzimidazole compounds are useful as antiviral agents.

40 Claims, No Drawings

CARBONYL-SUBSTITUTED 1-SULFONYLBENZIMIDAZOLES

CROSS REFERENCE TO RELATED APPLICATION

This application is a continuation-in-part of our co-pending application Ser. No. 608,415, filed Aug. 28, 1975, now abandoned.

BACKGROUND OF THE INVENTION

The incidence of viral upper respiratory disease is immense. It has been estimated that nearly a billion cases annually appear in the United States alone. Studies performed in England (Tyrell and Bynoe, 1966) indicated that 74 percent of persons having colds were infected with rhinoviruses. Because more than 80 strains of rhinoviruses are already identified, the development of a practical rhinovirus vaccine is not feasible, and chemotherapy appears to be the more desirable approach.

The ability of chemical compounds to suppress the growth of viruses in vitro is readily demonstrated by using a virus plaque suppression test similar to that described by Siminoff, Applied Microbiology, 9(1), 66(1961).

Certain antifungal 1-dimethylaminosulfonyl-2-aminobenzimidazole compounds have been disclosed in U.S. Pat. No. 3,853,908.

It is the purpose of this invention to provide novel benzimidazole compounds which inhibit the growth of viruses, particularly rhinoviruses, polio viruses, Coxsackie viruses, echo virus, and Mengo virus.

SUMMARY OF THE INVENTION

This invention concerns pharmacologically useful sulfonyl benzimidazole compounds having the formula

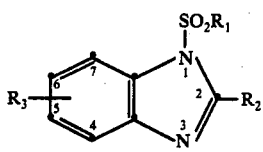

wherein $R_1$ is $C_1$-$C_5$ alkyl, $C_3$-$C_7$ cycloalkyl, phenyl, furyl, thienyl, thiazol-2-yl, 2-acetamido-4-methylthiazol-5-yl, 1,3,4-thiadiazol-2-yl, 2-methyl-1,3,4-thiadiazol-5-yl, 2-methylamino-1,3,4-thiadiazol-5-yl or $R_4R_5N$-, wherein $R_4$ and $R_5$ are independently $C_1$-$C_3$ alkyl or $R_4$ and $R_5$, when taken together with the nitrogen atom to which they are attached, are pyrrolidino, piperidino or morpholino;

$R_2$ is amino, formamido, acetamido, propionamido or butyramido;

$R_3$ is hydroxy, $C_2$-$C_8$ alkanoyloxy, phenylacetoxy, $\alpha$-$C_1$-$C_7$ alkyl-$\alpha$-hydroxybenzyl or benzoyloxy; or 1,3-dithiolan-2-yl, 1,3-dithian-2-yl, tetrazol-5-yl, 1-($C_1$-$C_4$ alkyl)tetrazol-5-yl, 1,3,4-oxadiazol-2-yl, or 2-($C_1$-$C_4$ alkyl)oxadiazol-5-yl; or

wherein $R_6$ is hydrogen, $C_1$-$C_7$ alkyl, $C_3$-$C_7$ cycloalkyl, ($C_3$-$C_7$ cycloalkyl)methyl, 1-($C_3$-$C_7$ cycloalkyl)ethyl, benzyl, phenyl or phenyl substituted by $C_1$-$C_4$ alkyl, $C_1$-$C_4$ alkoxy, chloro, bromo, iodo, nitro or trifluoromethyl; or $Z=C(R_6)$-, wherein Z is hydroxyimino, $C_1$-$C_4$ alkoxyimino, $C_1$-$C_4$ acyloxyimino, benzyloxyimino, benzoyloxyimino, hydrazono, thiocarbamylhydrazono, carboxymethoxyimino, methoxycarbonylhydrazono, ethoxycarbonylhydrazono, carbamylhydrazono, $C_1$-$C_4$ alkoxycarbonylethylcarbonyloxyimino, benzyloxycarbonylaminomethylcarbonyloxyimino, p-nitrobenzyloxycarbonylethylcarbonyloxyimino, phthalimidomethylcarbonyloxyimino, 2-(2-benzyloxycarbonyl-5-oxoisoxazolidin-4-yl)ethylcarbonyloxyimino or $C_1$-$C_7$ alkylidene; and $R_3$ is at the 5 or 6 position.

DETAILED DESCRIPTION AND PREFERRED EMBODIMENT

The present invention relates to new organic sulfonyl compounds that are useful as antiviral agents and to methods for their production. The compounds of the invention are prepared by reacting a tautomeric benzimidazole compound of the formula

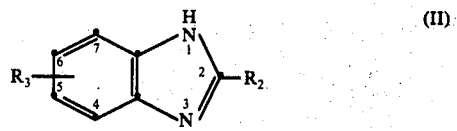

with a sulfonyl chloride compound having the formula $R_1SO_2Cl$ wherein $R_1$ and $R_3$ are as defined hereinabove, and $R_2$ is amino.

A preferred group of compounds are the compounds of formula (I) wherein $R_1$ is $C_1$-$C_4$ alkyl, $C_5$-$C_7$ cycloalkyl, thienyl, phenyl or $R_4R_5N$- wherein $R_4$ and $R_5$ are independently $C_1$-$C_3$ alkyl;

$R_2$ is defined as before;

$R_3$ is 1,3-dithiolan-2-yl, 1,3-dithian-2-yl, 1-($C_1$-$C_3$ alkyl)tetrazole-5-yl, 1,3,4-oxadiazol-2-yl, $\alpha$-$C_1$-$C_7$ alkyl-$\alpha$-hydroxybenzyl; or

wherein $R_6$ is hydrogen, $C_1$-$C_4$ alkyl, phenyl, or phenyl substituted by chloro, bromo, or iodo; or $Z=C(R_6)$-, wherein Z is hydroxyimino, $C_1$-$C_4$ alkoxyimino, $C_1$-$C_4$ acyloxyimino, benzyloxyimino, benzoyloxyimino, hydrazono, thiocarbamylhydrazono, carboxymethoxyimino, methoxycarbonylhydrazono, ethoxycarbonylhydrazono, carbamylhydrazono, $C_1$-$C_4$ alkoxycarbonylethylcarbonyloxyimino, benzyloxycarbonylaminomethylcarbonyloxyimino, p-nitrobenzyloxycarbonylethylcarbonyloxyimino, phthalimidomethylcarbonyloxyimino, 2-(2-benzyloxycarbonyl-5-oxoisoxazolidin-4-yl)ethylcarbonyloxyimino, or $C_1$-$C_7$ alkylidene; and $R_3$ is at the 5 or 6 position.

Another preferred group of compounds are the compounds of formula (I) wherein $R_1$ is defined as before;

$R_2$ is amino, formamido, acetamido, or propionamido;

$R_3$ is hydroxy, $C_2$-$C_8$ alkanoyloxy, phenylacetoxy, or benzoyloxy; or 1,3-dithiolan-2-yl, 1,3-dithian-2-yl, tetrazol-5-yl, 1-($C_1$-$C_4$ alkyl)tetrazol-5-yl, 1,3,4-oxadiazol-2-yl, or 2-($C_1$-$C_4$ alkyl)oxadiazol-5-yl; or

wherein $R_6$ is defined as before; or Z=C($R_6$)- wherein Z is hydroxyimino, $C_1$-$C_4$ alkoxyimino, hydrazono, thiocarbamylhydrazono, or carbamylhydrazono; and $R_3$ is at the 5 or 6 position.

The term "tautomeric benzimidazole" refers to a benzimidazole reagent which can be substituted at either nitrogen atom with a hydrogen atom. The benzimidazole reactant, unsubstituted on nitrogen and bearing a substituent group at the 5 position of the benzene moiety, has a corresponding tautomeric form wherein the substituent resides alternatively at the 6 position. The isomer mixture can be indicated by numbering the alternate positions as 5(6). As a consequence of such tautomerism, the reaction of a 5(6)-substituted benzimidazole with a sulfonyl chloride produces isomeric mixtures of 5(6)-substituted sulfonylbenzimidazoles.

The following definitions refer to the various terms used throughout this disclosure. The term "furan" refers to the furan radical attached at the 2 or 3 position. The term "thienyl" refers to the thiophene radical attached at the 2 or 3 position. The term "thiazol-2-yl" or "2-thiazole" refers to the thiazole radical attached at the 2 position. The term "1,3,4-thiadiazole-2-yl" or "thiadiazol-2-yl" refers to the 1,3,4-thiadiazole radical attached at the 2 position. The term "2-methyl-1,3,4-thiadiazol-5-yl" or "2-methylamino-1,3,4-thiadiazol-5-yl" refers to a 2-substituted-1,3,4-thiadiazole radical attached at the 5 position. The term "1,3-dithiolan-2-yl" refers to the 1,3-dithiolane radical attached at the 2 position. The term "1,3-dithian-2-yl" refers to the 1,3-dithiane radical attached at the 2-position. The term "1-($C_1$-$C_4$ alkyl)tetrazol-5-yl" refers to a 1-methyl-, 1-ethyl-, 1-propyl, or 1-butyltetrazole radical attached at the 5 position. The term "2-($C_1$-$C_4$ alkyl)oxadiazol-5-yl" refers to a 2-methyl-, 2-ethyl-, 2-propyl-, or 2-butyl-1,3,4-oxadiazole radical attached at the 5 position. The term "1,3,4-oxadiazol-2-yl" refers to the 1,3,4-oxadiazol radical attached at the 2-position.

The term "$C_1$-$C_8$ alkyl" refers to the straight and branched aliphatic radicals of one to eight carbon atoms including methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methyl-hexyl), 1-ethyl-2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl(1-methylheptyl), tert-octyl(1,1,3,3-tetramethylbutyl and the like. The term $C_1$-$C_8$ alkyl includes within its definition the terms "$C_1$-$C_3$ alkyl", "$C_1$-$C_4$ alkyl," "$C_1$-$C_5$ alkyl," and "$C_1$-$C_7$ alkyl."

The term "$C_1$-$C_8$ alkyl carbinol" refers to the straight and branched aliphatic alcohols of one to eight carbon atoms as exemplified in the term "$C_1$-$C_8$ alkyl."

The term "$C_3$-$C_7$ cycloalkyl" refers to the saturated alicyclic rings of three to seven carbon atoms such as cyclopropyl, methylcyclopropyl, cyclobutyl, cyclopentyl, cyclohexyl, 1-, 2-, 3- or 4-methylcyclohexyl and cycloheptyl. The term "($C_3$-$C_7$ cycloalkyl)methyl" refers to a methyl radical substituted with saturated alicyclic rings of three to seven carbon atoms as exemplified in the term "$C_3$-$C_7$ cycloalkyl," such as cyclopropylmethyl, cyclobutylmethyl, cyclopentylmethyl, cyclohexylmethyl, cycloheptylmethyl and the like. The term "1-($C_3$-$C_7$ cycloalkyl)ethyl" refers to ethyl radicals substituted on the carbon atom in the 1 position with saturated alicyclic rings of three to seven carbon atoms. The term "$C_3$-$C_7$ cycloalkylacetic acid" refers to acetic acid substituted on the carbon atom in the 2 position with saturated alicyclic rings of three to seven carbon atoms such as cyclopropaneacetic acid, cyclopentane acetic acid and the like. The term "2-($C_3$-$C_7$ cycloalkyl)propionic acid" refers to propionic acid substituted on the carbon atom in the 2 position with saturated alicyclic rings of three to seven carbon atoms such as 2-(cyclopropane)propionic acid, 2-(cyclohexane)propionic acid and the like.

The term "$C_2$-$C_8$ alkanoyl" refers to the straight chain aliphatic acyl radicals of two to eight carbon atoms and the branched aliphatic acyl radicals of four to five carbon atoms such as acetyl, propionyl, butyryl, 2-methylpropionyl, pentanoyl, hexanoyl, heptanoyl, octanoyl, and the like.

The term "$C_1$-$C_7$ alkylidene" refers to straight and branched radicals of one to seven carbon atoms such as methylene, ethylidene, propylidene, isopropylidene, butylidene, isobutylidene, 3-methyl-2-butylidene, n-hexylidene and the like.

The term "$C_1$-$C_4$ alkoxy" includes the straight and branched aliphatic ether radicals of one to four carbon atoms such as methoxy, ethoxy, propoxy, isopropoxy, butoxy, isobutoxy, sec-butoxy, and the like. The term "$C_1$-$C_4$ alkylamino" refers to the aliphatic primary and secondary amine radical of one to four carbon atoms derived from methylamine, ethylamine, propylamine, isopropylamine, butylamine, sec-butylamine, dimethylamine, methylethylamine, diethylamine, methylpropylamine and the like. The term "$C_1$-$C_4$ alkoxyamine" refers to the O-aliphatic hydroxylamine radical of one to four carbon atoms derived from hydroxylamine. Methoxyamine hydrochloride is available from commercial sources. Other hydroxylamine derivatives are available by (A) alkylation of acetone oxime by $C_1$-$C_4$ alkyl halides followed by acid hydrolysis, (B) alkylation of N-hydroxyphthalimide followed by hydrazinolysis or (C) alkylation of benzhydroxamic acid followed by acid hydrolysis.

The preferred reactants are benzimidazole compounds bearing 5(6)-substituents which will not react with the sulfonyl chloride reactant under the reaction conditions. The benzimidazole compound and the sulfonyl chloride are normally employed in approximately equimolar quantities, although an excess of either can be used if desired. The reaction can be carried out in any number of unreactive solvents, including acetone, tetrahydrofuran (THF), tertiary amides such as N,N-dimethylformamide (DMF), and chlorinated hydrocarbons such as dichloromethane, dichloroethane and chloroform. The reaction medium may also contain added base to serve as an acid-binding agent. Some examples of suitable bases for this purpose are pyridine, triethylamine, N-methylmorpholine, sodium bicarbonate, and sodium hydride. A preferred solvent medium for the reaction is acetone containing triethylamine or tetrahydrofuran with DMF containing sodium hydride as a base.

The reaction is best carried out at a temperature between room temperature and the reflux temperature of the solvent system empolyed. Preferably, the reaction is carried out at reflux temperature, and at this temperature, the reaction is substantially complete within 1 to 48 hours.

The product of the reaction is a 1-sulfonylbenzimidazole compound, hereinafter called the sulfonylbenzimidazole compound. The product may be isolated by filtering the reaction mixture and concentrating the filtrate to induce crystallization. Alternatively, the reaction mixture can be evaporated to dryness and the residue treated with a suitable solvent such as acetone or methanol to separate and remove any insoluble material. The solution containing the sulfonylbenzimidazole compound is concentrated to crystallize the product or it is evaporated to give a second residue, which is dissolved in methanol for example. The sulfonylbenzimidazole compound is recovered from the methanol by crystallization.

The reaction of the tautomeric benzimidazole compound and the sulfonyl chloride generally provides a 1:1 mixture of 5- and 6-substituted sulfonylbenzimidazole isomers. The isomers are separable by fractional crystallization or by column chromatography. Usually the 6-isomer crystallizes first from a solution of the mixture. For example, when ethyl 2-amino-5-benzimidazolecarboxylate is reacted with dimethylsulfamoyl chloride in acetone containing triethylamine, ethyl 1-dimethylaminosulfonyl-2-amino-6-benzimidazolecarboxylate crystallizes first from the reaction mixture. The acetone mother liquors contain predominantly ethyl 1-dimethylaminosulfonyl-2-amino-5-benzimidazolecarboxylate and residual amounts of the 6-isomer. The isomers can be identified by their nuclear magnetic resonance spectra in the phenyl proton region (7.0 to 8.3 ppm).

Some of the compounds of the invention can be prepared by performing chemical operations such as acylation, oxidation or reduction on the appropriate sulfonylbenzimidazole precursor. When the reactions are performed on a precursor which is an isomeric mixture of sulfonylbenzimidazoles, the isomeric products can be separated by methods such as fractional crystallization or chromatography.

It will be appreciated that advantageous chemical reactions can be performed at optional stages of product synthesis. The benzimidazole reactant can be chemically modified and then reacted with the appropriate sulfonyl chloride to provide the sulfonylbenzimidazole product. Alternatively, a sulfonylbenzimidazole intermediate can be prepared and then chemically modified to provide the final product. Suitable benzimidazole reactants are those having substituent groups which can be converted to the desired 5(6)-substituents either prior to or after reaction with the appropriate sulfonyl chloride. The ethyl esters of 2-substituted-5(6)-benzimidazolecarboxylic acids are especially suitable reactants because the ester function can be reacted to provide other intermediate compounds which can be converted to final products as described hereinafter.

The ethyl esters of the sulfonylbenzimidazolecarboxylic acid intermediates or isomeric mixtures thereof can be reacted with hydrazine in a carbinol solvent to yield the corresponding hydrazines. For example, ethyl 1-dimethylaminosulfonyl-2-amino-5(6)-benzimidazolecarboxylate can be refluxed with hydrazine hydrate in methanol to provide 1-dimethylaminosulfonyl-2-amino-5(6)-benzimidazolecarboxylic acid hydrazide. The hydrazide compounds can be converted to the corresponding 5(6)-[(2-substituted)oxadiazol-5-yl]sulfonylbenzimidazoles by heating at elevated temperatures with ortho esters such as ethyl orthoformate, ethyl orthoacetate or ethyl orthopropionate as illustrated in reaction scheme I. For example when 1-dimethylaminosulfonyl-2-acetamido-5(6)-benzimidazole carboxylic acid hydrazide is refluxed with ethyl orthoacetate the product is 1-dimethylaminosulfonyl-2-acetamido-5(6)-(2-methyloxadiazol-5-yl)-benzimidazole.

The ethyl esters of the 1-sulfonyl-2-substituted-5(6)-benzimidazolecarboxylic acids can be reduced chemically to provide the corresponding hydroxymethyl intermediates. For example, ethyl 1-dimethylaminosulfonyl-2-acetamido-5(6)-benzimidazolecarboxylate can be reduced with sodium bis(2-methoxyethoxy)-aluminum hydride in tetrahydrofuran to provide 1-dimethylaminosulfonyl-2-acetamido-5(6)-hydroxymethyl-benzimidazole. A better method reacts the sulfonyl chloride, $R_1SO_2Cl$, with the appropriate 2-substituted-5(6)-hydroxymethylbenzimidazole. The required 5(6)-hydroxymethylbenzimidazole reactant can be prepared from the corresponding ethyl 2-substituted-5(6)-benzimidazolecarboxylic acid by reduction with sodium bis(2-methoxyethoxy)-aluminum hydride in an aprotic solvent as described above. The preferred method for preparing large quantitites of the hydroxymethyl sulfonyl benzimidazole intermediates begins with 4-chloro-3-nitrobenzyl alcohol. The benzyl alcohol is ammoniated to give 4-amino-3-nitrobenzyl alcohol. The nitro alcohol is hydrogenated catalytically to yield 4-hydroxymethyl-o-phenylenediamine. The phenylenediamine is ring closed to provide the desired 2-substituted-5(6)-hydroxymethylbenzimidazole intermediate by methods known to the benzimidazole art.

Generally, the 5(6)-hydroxymethyl sulfonylbenzimidazole compounds are important as intermediates which can be converted to the corresponding 5(6)-formyl derivatives. The oxidation of the hydroxymethyl carbinol function to provide a carboxaldehyde compound with virus inhibiting properties is certainly unexpected. Furthermore the conversion of the carboxaldehyde function to a carbon-nitrogen double bond function in such a compound increases the antiviral activity to a considerable degree.

The sulfonylbenzimidazole carboxaldehyde compounds wherein $R_6$ is hydrogen can be prepared from the corresponding 1-sulfonyl-2-substituted-5(6)-hydroxymethylbenzimidazole compounds by oxidation of the hydroxymethyl group with Jones reagent, a solution of chromic acid and sulfuric acid in water. For example, 1-dimethylaminosulfonyl-2-amino-5(6)-hydroxymethyl-benzimidazole yields 1-dimethylaminosulfonyl-2-amino-5(6)-formylbenzimidazole after oxidation with Jones reagent. The sulfonylbenzimidazole carboxaldehyde compounds can be converted to their 5(6)-hydrazonomethylene, 5(6)-carbamylhydrazonomethylene, 5(6)-thiocarbamylhydrazonomethylene, 5(6)-hydroxyiminomethylene or 5(6)-($C_1$-$C_4$)alkyloxyiminomethylene derivatives by reacting them with hydrazine, semicarbazide, thiosemicarbazide, hydroxylamine, or $C_1$-$C_4$ alkoxyamines in the usual manner since the carboxaldehyde function is quite reactive. The 5(6)-(1,3-dithiolan-2-yl) and 5(6)-(1,3-dithan-2-yl) derivatives can be obtained by reacting the 5-(6)-formyl sulfonylbenzimidazole compounds with 1,2-ethanedithiol or 1,3-propanedithiol respectively in the presence of boron trifluoride etherate and recovering the cyclic thioacetal products.

When the oxime and oxime derivatives are prepared, the products are usually mixtures of the syn and anti isomers. The proportion of the anti isomer can be increased by conventional methods, e.g. fractional crystallization or high pressure chromatography. As the anti isomer is more active biologically this enrichment process is useful. These carbonyl reactions are illustrated in Reaction Scheme I.

Reaction Scheme I

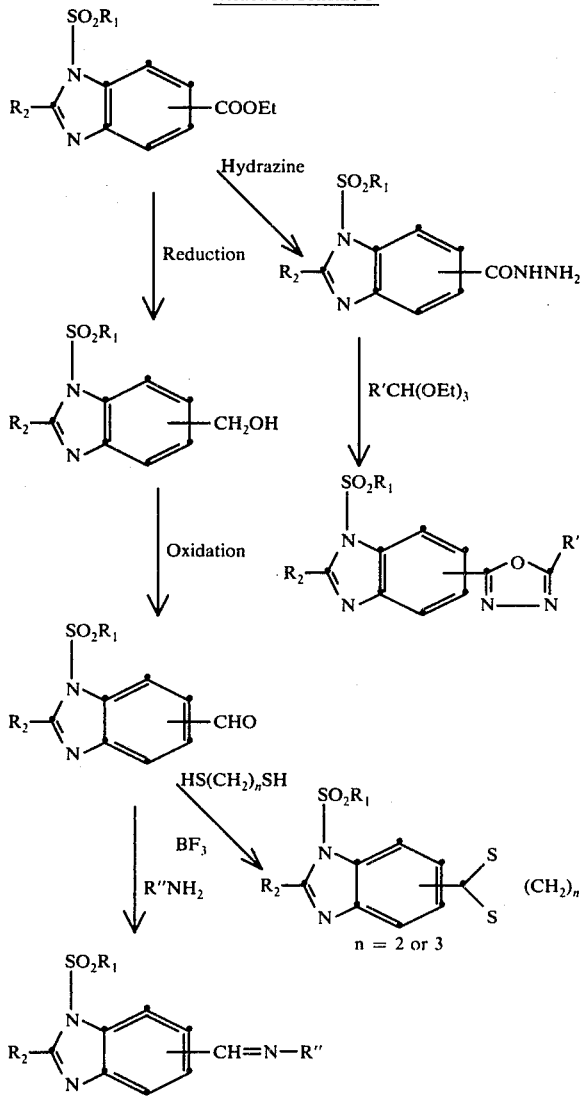

R' = H, $C_1-C_4$ alkyl
R" = OH, $OC_1-C_4$ alkyl, $NH_2$, $NHC(O)NH_2$, $NHC(S)NH_2$ The 5(6)-keto sulfonylbenzimidazole compounds wherein $R_3$ is $R_6CO$ can be prepared from the corresponding 5(6)-keto benzimidazoles by reaction with the sulfonyl chloride, $R_1SO_2Cl$. The keto benzimidazole reactant can be prepared from the appropriate keto o-phenylenediamine by methods known to the benzimidazole art. Belgian published application No. 93791 discloses the preparation of keto o-phenylenediamines of the formula

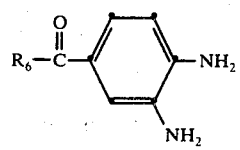

wherein $R_6$ is lower alkyl, cycloalkyl, phenyl or phenyl substituted by halogen, lower alkyl or lower alkoxy. The method of preparation involves the ammonolysis and reduction of a 4-halo-3-nitrophenyl ketone which is prepared by the Friedel-Crafts reaction of either (1) a 4-halo-3-nitrobenzoyl chloride with an appropriate hydrocarbon or (2) a halobenzene with an appropriate acid chloride followed by aromatic nitration. Such methods make available the required keto o-phenylenediamines wherein $R_6$ in the formula above is additionally $C_3-C_7$ cycloalkyl, $(C_3-C_7$ cycloalkyl)methyl, 1-$(C_3-C_7$ cycloalkyl)ethyl or benzyl. Alternatively the keto benzimidazole reactants can be prepared from acetanilide by a Friedel-Crafts acylation with the appropriate derivative of a $C_2-C_8$ alkanoic acid, $C_3-C_7$ cycloalkyl carboxylic acid, $C_3-C_7$ cycloalkylacetic acid, 2-$(C_3-C_7$ cycloalkyl)propionic acid, phenylacetic acid, benzoic acid or substituted benzoic acid. The resulting 4-keto acetanilide is nitrated to give a 2-nitro-4-ketoacetanilide. The acetanilide is hydrolyzed to give a 2-nitro-4-ketoaniline. The nitroaniline is catalytically hydrogenated to yield a 4-keto-o-phenylenediamine which is ring closed to provide the appropriate 2-substituted-5(6)-ketobenzimidazole. The following embodiment illustrates in principle the preparation of a 5(6)-keto sulfonylbenzimidazole compound. 4-Propionylacetanilide is nitrated at 0° C. to yield 2-nitro-4-propionylacetanilide. The acetanilide is hydrolyzed and catalytically hydrogenated to give 4-propionyl-o-phenylenediamine. The phenylenediamine is reacted with cyanogen bromide to give 2-amino-5(6)-propionylbenzimidazole. The propionylbenzimidazole is reacted with dimethylsulfamoyl chloride to provide 1-dimethylaminosulfonyl-2-amino-5(6)-propionylbenzimidazole. These methods make available the 5(6)-$(C_2-C_8)$alkanoyl, 5(6)-$(C_3-C_7)$cycloalkylcarbonyl, 5(6)-$(C_3-C_7)$cycloalkylacetyl, 5(6)-[2-$(C_3-C_7$ cycloalkyl)propionyl], 5(6)-phenylacetyl, 5(6)-benzoyl or the 5(6)-substituted-benzoyl sulfonylbenzimidazole compounds. The 5(6)-keto sulfonylbenzimidazole compounds are represented by the formula

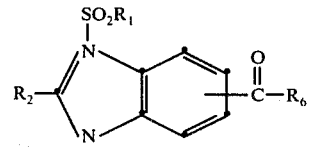

wherein $R_6$ is $C_1-C_7$ alkyl, $C_3-C_7$ cycloalkyl, $(C_3-C_7$ cycloalkyl)methyl, 1-$(C_3-C_7$ cycloalkyl)ethyl, benzyl, phenyl or phenyl substituted by $C_1-C_4$ alkyl, $C_1-C_4$ alkoxy, chloro, bromo, iodo, nitro or trifluoromethyl, and $R_1$ and $R_2$ are as defined previously. As with the sulfonylbenzimidazole carboxaldehyde compounds, the 5(6)-keto sulfonylbenzimidazole compounds can be reacted with hydrazine, semicarbazide, thiosemicarbazide, hydroxylamine or $C_1$-$C_4$ alkoxyamines to provide their hydrazone, semicarbazone, thiosemicarbazone, oxime, or $C_1$-$C_4$ alkoxyamine derivatives.

The compounds of formula I wherein $R_3$ is Z=$C(R_6)$— wherein Z is an acyloxyamine are prepared by reacting the corresponding hydroxyiminobenzimidazole with the appropriate acylating agent (such as an anhydride).

The compounds of formula I wherein $R_3$ is Z=$C(R_6)$— wherein Z is an alkoxyamine are prepared by reacting the appropriate ketobenzimidazole with an alkoxyamine, or by alkylating the corresponding hydroxyiminobenzimidazole (suitable alkylating agents are an alkali metal alkoxide and alkyl halide). The benzyloxyamines are prepared in a corresponding manner.

The compounds of formula I wherein $R_3$ is Z=$C(R_6)$— wherein Z is an alkoxyamine are prepared by reacting the appropriate ketobenzimidazole with an alkoxyamine, or by alkylating the corresponding hydroxyiminobenzimidazole (suitable alkylating agents are an alkali metal alkoxide and alkyl halide). The benzyloxyamines are prepared in a corresponding manner.

The compounds of formula I wherein $R_3$ is Z=$C(R_6)$ — wherein Z is $C_1$-$C_4$ alkoxycarbonylethylcarbonyloxyamine are prepared by reacting the appropriate hydroxyiminobenzimidazole with a carboalkoxypropionyl halide.

The compounds of formula I wherein $R_3$ is Z=$C(R_6)$— wherein Z is p-nitrobenzyloxycarbonylethylcarbonyloxyamine are prepared by reacting the appropriate hydroxyiminobenzimidazole with p-nitrobenzyloxycarbonylpropionyl halide. Succinic anhydride and p-nitrobenzyl alcohol in dimethylformamide and reflux provides the p-nitrobenzyloxycarbonylpropionic acid, followed by making the acid chloride using oxalyl chloride and pyridine.

The compounds of formula I wherein $R_3$ is Z=$C(R_6)$— wherein Z is benzyloxycarbonylaminomethylcarbonyloxyamine are prepared by reacting the appropriate hydroxyiminobenzimidazole with benzyloxycarbonylaminomethylcarboxylic acid chloride.

The compounds of formula I wherein $R_3$ is Z=$C(R_6)$— wherein Z is phthalimidomethylcarbonyloxyamine are prepared by reacting the appropriate hydroxyiminobenzimidazole with phthalimidomethylcarboxylic acid chloride.

The compounds of formula I wherein $R_3$ is Z=$C(R_6)$— wherein Z is 2-(2-benzyloxycarbonyl-5-oxoisoxazolidin-4-yl)ethylcarbonyloxyamine are prepared by reacting the appropriate hydroxyiminobenzimidazole with 3-(3-benzyloxycarbonyl-5-oxoisoxazolidin-4-yl)propionic acid chloride. The preparation of 3-(3-benzyloxycarbonyl-5-oxoisoxazolidin-4-yl)propionic acid is discussed by Masumi Itoh, Chem. Pharm. Bull. 17 (8) 1679–1686 (1969).

However the keto carbonyl function is less reactive than the carboxaldehyde function. The keto function can be activated by protonating the sulfonylbenzimidazole compound under acidic conditions and subsequently carbonnitrogen double bond formation occurs readily. These nitrogen derivatives are represented by the formula

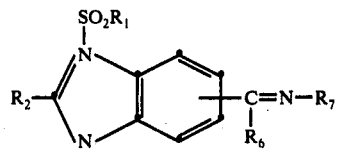

wherein $R_7$ is hydroxy, $C_1$-$C_4$ alkoxy, $C_1$-$C_4$ acyloxy, benzyloxy, benzoyloxy, amino, thiocarbamylamino, carboxymethoxy, methoxycarbonylamine, ethyloxycarbonylamino, carbamylamino, $C_1$-$C_4$ alkoxycarbonylethylcarbonyloxy, benzyloxycarbonylaminomethylcarbonyloxy, p-nitrobenzyloxycarbonylethylcarbonyloxy, phthalimidomethylcarbonyloxy, 2-(2-benzyloxycarbonyl-5-oxoisoxazolidin-4-yl)ethylcarbonyloxy, and $R_1$, $R_2$, and $R_6$ are as defined previously. When $R_6$ is hydrogen, the nitrogen derivatives are those of the 5-(6)-formyl sulfonylbenzimidazole compounds.

The nitrogen functions are named according to the carbonyl reagent from which they are derived as follows:

| carbonyl reagent | N-function (name) |
| --- | --- |
| hydroxylamine | hydroxyimino |
| methoxyamine | methoxyimino |
| ethoxyamine | ethoxyimino |
| propoxyamine | propoxyimino |
| butoxyamine | butoxyimino |
| hydrazine | hydrazono |
| semicarbazide | carbamylhydrazono |
| thiosemicarbazide | thiocarbamylhydrazono |
| acyloxyamine | acyloxyimino |
| benzyloxyamine | benzyloxyimino |
| benzoyloxyamine | benzoyloxyimino |
| carboxymethoxyamine | carboxymethoxyimino |
| methoxycarbonylhydrazine | methoxycarbonylhydrazono |

The $C_1$-$C_7$ alkylidene derivatives are prepared from the corresponding (α-hydroxy-α-$C_1$-$C_7$ alkyl)benzyl derivatives by dehydration with p-toluenesulfonic acid.

The (α-hydroxy-α-$C_1$-$C_7$ alkyl)benzyl derivatives and the (α-hydroxy-α-$C_1$-$C_7$ branched alkyl)benzyl derivatives are prepared by reacting the corresponding keto derivative with the appropriate Grignard reagent followed by hydrolysis.

The sulfonylbenzimidazole compounds wherein $R_3$ is a heterocyclic moiety such as 1,3-dithiane, 1,3-dithiolane, oxadiazole or tetrazole can be prepared by the following methods. The following embodiment illustrates in principle the preparation of the 5(6)-(1-alkyltetrazol-5-yl) slfonylbenzimidazole compounds of the invention. The process begins by preparing the desired 2-substituted-5-(6)-(1-alkyltetrazol-5-yl)benzimidazole reactant as illustrated by the following example. 4-Aminobenzonitrile is acetylated and nitrated to give 3-nitro-4-acetamidobenzonitrile. The benzonitrile is reacted with sodium azide in dimethylformamide in the presence of ammonium chloride to yield 5-(3-nitro-4-acetamidophenyl)tetrazole. The tetrazole moiety is alkylated with methyl iodide in acetone and triethylamine to provide 1(2)-methyl-5-(3-nitro-4-acetamidophenyl)-tetrazole as an isomeric mixture. The tetrazole mixture is hydrolyzed with concentrated sulfuric acid at room temperature for several hours to yield 1(2)-methyl-5-(3-nitro-4-aminophenyl)tetrazole. The nitro group of the benzene moiety is hydrogenated in ethanol-ethyl acetate at 30° C. in the presence of palladium-on-carbon to give 1(2)-methyl-5-(3,4-diaminophenyl)tetrazole. The diaminophenyltetrazole is reacted with cyanogen bromide in methanol-water to yield essentially one methyl isomer, 2-amino-5(6)-(1-methyltetrazol-5-yl)benzimidazole. When the benzimidazole is reacted with dimethylsulfamoyl chloride in acetone in the presence of triethylamine, the product is 1-dimethylaminosulfonyl-2-amino-5(6)-(1-methyltetrazol-5-yl)benzimidazole. by employing the appropriate 2-substituted-5(6)-(1-alkyltetrazol-5-yl)benzimidazole reactants and sulfonyl chlorides as described above, other 5-(6)-(1-alkyltetrazol-5-yl)sulfonylbenzimidole compounds of the invention can be prepared.

The 5(6)-(tetrazol-5-yl)sulfonylbenzimidazale compounds are useful for preparing the corresponding 5(6)-(oxadiazol-5-yl)sulfonylbenzimidazole compounds by thermal rearrangement. In the preparation of the tetrazole compounds, 5-(3-nitro-4-acetamidophenyl)tetrazole is acylated to yield a 1(2)-acyl-5-(3-nitro-4-acetamidophenyl)tetrazole. The ultimate product from such a reactant is a 5(6)-[1(2)-acyltetrazol-5-yl]sulfonylbenzimidazole compound which upon thermolysis at elevated temperatures yields the corresponding 5(6)-(2-substituted-oxadiazol-5-yl)sulfonylbenzimidazole compounds.

The sulfonylbenzimidazole compounds wherein $R_3$ is hydroxy can be prepared from the corresponding 5(6)hydroxybenzimidazole reactants. The preparation of the required hydroxybenzimidazole compounds begins with the reduction of 4-methoxy-2-nitroaniline to the corresponding 4-methoxy-o-phenylenediamine. The phenylenediamine is ring closed to provide a 2-substituted-5(6)-methoxybenzimidazole by methods known to the benzimidazole art. The methyl ether is cleaved with hydrobromic acid to give a 2-substituted-5(6)-hydroxybenzimidazole. The hydroxybenzimidazole is reacted with the appropriate sulfonyl chloride to provide the required 2-substituted-5(6)-hydroxy sulfonylbenzimidazole compounds.

The phenolic hydroxyl function of the 5(6)-hydroxy sulfonylbenzimidazole compounds can be reacted with the anhydrides or chlorides of $C_2$-$C_8$ alkanoic acids, phenylacetic acid or benzoic acid in an aprotic solvent to provide the corresponding esters. The ester products derived from the 5(6)-hydroxy sulfonylbenzimidazole reactants are respectively the 5(6)-($C_2$-$C_8$)alkanoyloxy, 5(6)-phenylacetoxy or 5(6)-benzoyloxy sulfonylbenzimidazole compounds. Alternatively the hydroxy sulfonylbenzimidazole compounds can be esterified with the appropriate acid reactant in the presence of 1,1'-carbonyldiimidazole in dimethylformamide.

The benzimidazole compounds which are required as starting materials in the foregoing process can be prepared according to a variety of methods known to the benzimidazole art. The preparation of a variety of benzimidazoles is well documented in Weissberger's *The Chemistry of Heterocyclic Compounds, Imidazole and Its Derivatives*, Interscience Publishers Co., New York, 1953. The 2-aminobenzimidazole reactants can be prepared by cyclizing the appropriate o-phenylenediamines with cyanogen bromide as described by Buttle, et al., Bio. Chem. J. 32, 1101 (1938) and British Pat. 551,524. Acylation of the 2-aminobenzimidazole reactant with acetic or propionic anhydride provides the 2-acetamido-or 2-propionamidobenzimidazoles. The 2-formamidobenzimidazole reagents can be obtained by reacting the appropriate 2-aminobenzimidazole with the mixed anhydride obtained from formic acid and acetic anhydride. Alternatively, the 2-acylamino sulfonylbenzimidazole compounds can be prepared from the corresponding 2-amino sulfonylbenzimidazole compounds by acylation as described hereinabove. Ethyl 2-amino-5(6)-benzimidazolecarboxylate is described by Paget, et al., J. Med. Chem. 12, 1010 (1969). Illustrative of such benzimidazole compounds which can be reacted with the appropriate sulfonyl chlorides are the 2-amino-, 2-formamido, 2-acetamido- or 2-propionamidobenzimidazoles substituted in the 5(6) position with hydroxy, hydroxymethyl, ethoxycarbonyl, formyl, keto, and the like.

Among the sulfonyl chloride compounds which are required as reactants, methanesulfonyl chloride (mesyl chloride), isopropylsulfonyl chloride, dimethylsulfamoyl chloride, benzenesulfonyl chloride, 2-thiophenesulfonyl chloride, and 2-acetamido-4-methyl-5-thiazolesulfonyl chloride are commercially available. The preparation of 3-thiophenesulfonyl chloride and 2(or 3)-furansulfonyl chloride is described by Arcoria et al., J. Org. Chem., 39, 1689 and 3595 (1974). 2-Thiazolesulfonyl chloride, 2-thiadiazolesulfonyl chloride, 2-methyl-5-thiadiazolesulfonyl chloride and 2-methylamino-5-thiadiazolesulfonyl chloride are available from 2-thiazolethiol, 2-thiadiazolethiol, 2-methyl-5-thiadiazolethiol and 2-methylamino-5-thiadiazolethiol respectively by oxidation of the thiol function with bromine or chlorine in aqueous solution. Other $C_1$-$C_5$ alkyl and $C_3$-$C_7$ cycloalkyl sulfonyl chlorides can be prepared by the chlorination of the appropriate alkyl thiol or by reacting sulfuryl chloride with sodium alkyl sulfonates derived from the corresponding carbinols and sulfuric acid. The N,N-dialkylsulfamoyl chlorides can be prepared as described by Bindely et al., J. Am. Chem. Soc. 61, 3250 (1939), by reacting a secondary amine salt with sulfuryl chloride. Alternatively, they can be prepared by reacting a chloramine compound of the formula

$R_4R_5N$-Cl with a sulfur dioxide at a temperature of $-5°$ to $30°$ C. The chloramine compounds are prepared by reacting the corresponding secondary amines with antimony pentachloride, sodium hypochlorite or sulfuryl chloride.

Further illustrative of the sulfonyl chlorides which can be reacted with the benzimidazole compounds are ethyl-, propyl-, isopropyl-, butyl-, isobutyl-, sec-butyl, tert-butyl, amyl-, isoamyl-, sec-isoamyl-, and tert-amyl-sulfonyl chloride in addition to cyclobutyl-, cyclopentyl-, cyclohexyl-, and cycloheptylsulfonylchloride.

Other sulfamoyl chlorides which can be employed are diethyl-, dipropyl-, N-methyl-N-ethyl-, N-methyl-N-propyl-, N-ethyl-N-isopropyl-, N-ethyl-N-isopropyl, N-propyl-N-isopropyl-, diisopropyl-, pyrrolidino-, piperidino-, and morpholinosulfamoyl chloride.

For consistency in nomenclature, the sulfonylbenzimidazole compounds will be named as sulfonyl derivatives. For example, the product of the reaction of dimethylsulfamoyl chloride and ethyl 2-amino-5-benzimidazolecarboxylate is named ethyl 1-dimethylaminosulfonyl-2-amino-5(6)-benzimidazolecarboxylate rather than ethyl 1-dimethylsulfamoyl-2-amino-5(6)-benzimidazolecarboxylate. The compounds of the invention were tested by the following methods.

Test Methods

African green monkey kidney cells (BSC-1) or Hela cells (5-3) were grown in 25 cc. Falcon flasks at 37° C. in medium 199 with 5 percent inactivated fetal bovine serum (BFS), penicillin (150 units 1 ml.) and streptomycin (150 mcg./ml.). When confluent monolayers were formed, the supernatant growth medium was removed and 0.3 ml. of an appropriate dilution of virus (echo, Mengo, Coxsackie, polio or rhinovirus) was added to each flask. After absorption for one hour at room temperature, the virus infected cell sheet was overlaid with a medium comprising one part of 1 percent Ionagar No. 2 and one part double strength medium 199 with FBS, penicillin, and streptomycin which contains drug at concentrations of 100, 50, 25, 12, 6, 3 and 0 micrograms per milliliter (mcg./ml.). The flask containing no drug served as the control for the test. The stock solutions of sulfonylbenzimidazole compounds were made up in dimethylsulfoxide dilution at a concentration of $10^4$ mcg./ml. The flasks were incubated for 72 hours at 37° C. for polio, Coxsackie, echo, and Mengo virus and 120 hours at 32° C. for rhinovirus. Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque reduction, or percent inhibition. Alternatively, the drug concentration which inhibits plaque formation by 50 percent can be used as a measure of activity. The 50 percent inhibition is indicated by the symbol $I_{50}$.

Test results are expressed in terms of Polio virus type I inhibition because the virus is easy to grow and consistent test results are obtained. However, the activity of the preferred compounds was confirmed against other virus cultures such as Coxsackie (A9, A21, B5), echovirus (strains 1-4), Mengo, rhinovirus (25 strains) and Polio (type I, II, III). Test results for various sulfonylbenzimidazole compounds are summarized in Table I below where column 1 gives the Example number from the previous chemical examples, column 2 gives the 5(6)-position of the corresponding benzimidazole product, and columns 3-10 indicate the percentage virus plaque reduction at drug dilutions from 0.75-100 micrograms per milliliter (mcg./ml.).

Table I

Polio I Plaque Reduction of 1-Substituted-sulfonyl-2-amino-5(6)-Substituted-Benzimidazoles

| Example No. | Isomer | Drug Concentration (mcg./ml.)* | | | | | | | | |
|---|---|---|---|---|---|---|---|---|---|---|
| | | 100 | 50 | 25 | 12 | 6 | 3 | 1.5 | 0.75 | |
| 13 | 5(6) | 100 | 95 | 54 | 0 | 0 | 0 | 0 | 0 | Percent |
| 14 | 5(6) | 100 | 100 | 100 | 100 | 100 | 100 | 81 | 15 | Plaque |
| 15 | 5(6) | Toxic | 97 | 87 | 59 | 37 | 24 | 0 | 0 | Reduction |
| 16 | 5(6) | 100 | 100 | 100 | 100 | 99 | 83 | 47 | 25 | |
| 29 | 6 | Toxic | 100 | 100 | 100 | 100 | 100 | 100 | | |
| 18 | 5(6) | 100 | 100 | 100 | 100 | 100 | 99 | 54 | 27 | |
| 18 | 6 | 100 | 100 | 100 | 100 | 100 | 76 | 41 | | |
| 19 | 5(6) | 100 | 100 | 100 | 100 | 98 | 68 | 15 | 0 | |
| 55 | 5(6) | 100 | 100 | 100 | 100 | 100 | 90 | 27 | 19 | |
| 53 | 5(6) | 100 | 100 | 100 | 100 | 100 | 90 | 52 | 27 | |
| 54 | 6 | 100 | 100 | 100 | 100 | 100 | 71 | 39 | 0 | |
| 21 | 6 | 100 | 100 | 100 | 100 | 66 | 11 | 0 | 0 | |
| 25 | 6 | 100 | 100 | 100 | 100 | 94 | 46 | 15 | 2 | |
| 22 | 5 | — | 100 | 100 | 92 | 95 | 50 | 0 | 0 | |
| 22 | 6 | 100 | 100 | 100 | 99 | 96 | 93 | 70 | 33 | |
| 20 | 5(6) | 100 | 100 | 100 | 100 | 99 | 64 | 25 | 0 | |
| 23 | 5(6) | sl. toxic | 100 | 100 | 100 | 100 | 88 | 37 | 17 | |
| 24 | 6 | 100 | 100 | 100 | 100 | 100 | 100 | 64 | 24 | |
| 26 | 6 | 100 | 100 | 100 | 95 | 86 | 51 | 17 | 6 | |
| 27 | 5(6) | 100 | 100 | 33 | 0 | 0 | 0 | 0 | 0 | |
| 28 | 6 | Toxic | 100 | 100 | 100 | 94 | 61 | 0 | 0 | |
| 30 | 5 | Toxic | Toxic | Toxic | 100 | 91 | 59 | 0 | 0 | |
| 30 | 6 | Toxic | mod. toxic | sl. toxic | 100 | 100 | 100 | 99 | 84 | |
| 31 | 5(6) | Toxic | sl. | 100 toxic | 100 | 100 | 96 | 45 | 8 | |
| 17 | 5(6) | 100 | 100 | 94 | 66 | 30 | 16 | 0 | 0 | |
| 32 | 6 | Toxic | Toxic | Toxic | 100 | 100 | 100 | 80 | 40 | |
| 33 | 5(6) | Toxic | Toxic | Toxic | mod. toxic | 80 | 48 | 29 | 12 | |
| 34 | 5 | Toxic | Toxic | Toxic | 100 | 100 | 100 | 100 | 100 | |
| 34 | 6 | sl. toxic | 100 | 100 | 100 | 100 | 100 | 100 | 100 | |
| 35 | 5(6) | Toxic | Toxic | sl. toxic | 100 | 100 | 100 | 100 | 100 | |
| 37 | 6 | 100 | 100 | 100 | 100 | 100 | 100 | 97 | 81 | |
| 38 | 5(6) | Toxic | mod. toxic | sl. toxic | sl. toxic | 100 | 95 | 40 | 0 | |
| 39 | 6 | Toxic | Toxic | mod. toxic | mod. toxic | 100 | 100 | 100 | 100 | |
| 40 | 6 | Toxic | sl. toxic | 100 | 100 | 100 | 88 | 64 | 43 | |
| 41 | 6 | 36 | 17 | 6 | 8 | 10 | 3 | 0 | 0 | |
| 42 | 6 | Toxic | Toxic | sl. toxic | 100 | 100 | 100 | 100 | 100 | |
| 43 | 6 | mod. toxic | mod. toxic | 100 | 100 | 100 | 81 | 57 | 19 | |
| 44 | 6 | Toxic | 100 | 100 | 100 | 100 | 100 | 100 | 100 | |
| 45 | 6 | 100 | 100 | 100 | 100 | 100 | 100 | 100 | 100 | |
| 47 | 6 | Toxic | mod. toxic | 100 | 100 | 100 | 100 | 100 | 100 | |
| 49 | 5(6) | 100 | 100 | 100 | 100 | 100 | 100 | 97 | 51 | |
| 50 | 5(6) | Toxic | mod. toxic | sl. toxic | 100 | 95 | 66 | 29 | 19 | |
| 36 | 5(6) | Toxic | sl. toxic | 100 | 100 | 100 | 100 | 76 | 35 | |
| 48 | 6 | mod. | mod. | 100 | 100 | 100 | 100 | 100 | 100 | |

Table I-continued
Polio I Plaque Reduction of 1-Substituted-sulfonyl-2-amino-5(6)-Substituted-Benzimidazoles

| Example No. | Isomer | \multicolumn{8}{c}{Drug Concentration (mcg./ml.)*} |
| --- | --- | --- | --- | --- | --- | --- | --- | --- | --- |
| | | 100 | 50 | 25 | 12 | 6 | 3 | 1.5 | 0.75 |
| 51 | 6 | toxic | toxic | 93 | 67 | 18 | 0 | 0 | 0 |
| | | 100 | 100 | | | | | | |
| 52 | 5(6) | 100 | 100 | 91 | 72 | 53 | 34 | 35 | 22 |
| 62 | 5(6) | Toxic | sl. toxic | 100 | 100 | 100 | 100 | 100 | 100 |
| 63 | 5(6) | 100 | 100 | 100 | 100 | 100 | 100 | 100 | 100 |
| 64 | 5(6) | Toxic | 100 | 100 | 100 | 100 | 100 | 100 | 100 |
| 65 | 5(6) | Toxic | Toxic | sl. toxic | 100 | 100 | 100 | 100 | 100 |
| 66 | 5(6) | Toxic | sl. toxic | 100 | 100 | 100 | 100 | 100 | 100 |
| 67 | 5(6) | mod. toxic | sl. toxic | 100 | 100 | 100 | 100 | 100 | 100 |
| 68 | 5(6) | Toxic | sl. toxic | 100 | 100 | 100 | 100 | 100 | 100 |
| 69 | 5(6) | Toxic | mod. toxic | sl. toxic | 100 | 100 | 100 | 100 | 100 |
| 70 | 5(6) | sl. toxic | 100 | 100 | 100 | 100 | 100 | 100 | 100 |
| 76 | anti-6 | Toxic | sl. toxic | 100 | 100 | 100 | 100 | 100 | 100 |
| 76 | syn-6 | Toxic | mod. toxic | sl. toxic | 100 | 100 | 100 | 100 | 100 |
| 71 | 6 | mod. toxic | 100 | 100 | 96 | 62 | 35 | 0 | 0 |
| 72 | 6 | 100 | 100 | 100 | 100 | 100 | 100 | 100 | 97 |
| 73 | 6 | Toxic | mod. toxic | sl. toxic | 100 | 88 | 54 | 2 | 0 |
| 74 | 6 | Toxic | Toxic | Toxic | 100 | 100 | 100 | 100 | 100 |

Preferred sulfonylbenzimidazole compounds coming within the scope of this invention are those wherein $R_2$ is amino, $R_3$ is 1,3-dithiolan-2-yl, 1,3-dithian-2-yl, oxadiazol-2-yl or substituted tetrazol-5-yl, $C_1$–$C_3$ alkyl, $R_6$ is hydrogen, phenyl or phenyl substituted by $C_1$–$C_4$ alkyl, $C_1$–$C_4$ alkoxy, halogen (chloro, bromo, iodo), nitro or trifluoromethyl, and $R_7$ is hydroxy, amino, ureido or thioureido. Especially preferred are the oxime derivatives of the 5(6)-benzoyl sulfonylbenzimidazole compounds ($R_6$ is phenyl or substituted phenyl and $R_7$ is hydroxy). Illustrative of such preferred compounds are the following:

1-dimethylaminosulfonyl-2-amino-5(6)-(4-chlorobenzoyl)benzimidazole,
1-dimethylaminosulfonyl-2-amino-5(6)-(α-hydroxyimino-4-chlorobenzyl)benzimidazole,
1-dimethylaminosulfonyl-2-amino-5(6)-(α-methoxyiminobenzyl)benzimidazole,
1-dimethylaminosulfonyl-2-amino-5(6)-(α-thiocarbamylhydrazonobenzoyl)benzimidazole,
1-(N-methyl-N-ethylaminosulfonyl)-2-amino-5(6)-(α-methoxyimino-4-trifluoromethylbenzyl)benzimidazole,
1-dipropylaminosulfonyl-2-amino-5(6)-(3-nitrobenzoyl)benzimidazole,
1-(N-methyl-N-propylaminosulfonyl)-2-amino-5(6)-(α-hydroximino-3-methoxybenzyl)benzimidazole,
1-diethylaminosulfonyl-2-amino-5(6)-(α-hydrazono-4-methylbenzyl)benzimidazole,
1-dimethylaminosulfonyl-2-amino-5(6)-(α-propoxyimino-4-ethoxybenzyl)benzimidazole,
1-(N-ethyl-N-propylaminosulfonyl)-2-amino-5(6)-(α-ethoxyimino-3-bromobenzyl)benzimidazole,
1-dimethylaminosulfonyl-2-amino-5(6)-(α-carbamylhydrazono-3-propylbenzyl)benzimidazole,
1-(N-methyl-N-propylaminosulfonyl)-2-amino-5(6)-(α-hydrazono-3-butoxybenzyl)benzimidazole,
1-diethylaminosulfonyl-2-amino-5(6)-(α-methoxyimino-4-nitrobenzyl)benzimidazole,
1-(N-methyl-N-propylaminosulfonyl)-2-amino-5(6)-(α-hydrazono-3-trifluoromethylbenzyl)benzimidazole,
1-dipropylaminosulfonyl-2-amino-5(6)-(α-thiocarbamylhydrazono-3-butoxybenzyl)benzimidazole,
1-(N-methyl-N-ethylaminosulfonyl)-2-amino-5(6)-(α-hydroxyimino-3-bromobenzyl)benzimidazole,
1-dimethylaminosulfonyl-2-amino-5(6)-(α-hydroxyimino-4-iodobenzyl)benzimidazole,
1-(N-methyl-N-propylaminosulfonyl)-2-amino-5(6)-(3-ethoxybenzoyl)benzimidazole,
1-diethylaminosulfonyl-2-amino-5(6)-(4-trifluoromethylbenzoyl)benzimidazole,
1-(N-ethyl-N-propylaminosulfonyl)-2-amino-5(6)-(4-ethylbenzoyl)benzimidazole,
1-(N-methyl-N-ethylaminosulfonyl)-2-amino-5(6)-(3-propoxybenzoyl)benzimidazole,
1-dimethylaminosulfonyl-2-amino-5(6)-(3,4-dichlorobenzoyl)benzimidazole,
1-dimethylaminosulfonyl-2-amino-5(6)-(α-hydroxyimino-3,4-dichlorobenzyl)benzimidazole,
1-(N-methyl-N-propylaminosulfonyl)-2-amino-5(6)-(4-butylbenzoyl)benzimidazole,
1-dipropylaminosulfonyl-2-amino-5(6)-(3-butoxybenzoyl)benzimidazole,
1-(N-ethyl-N-propylaminosulfonyl)-2-amino-5(6)-(3-chloro-4-methoxybenzoyl)benzimidazole,
1-(N-methyl-N-ethylaminosulfonyl)-2-amino-5(6)-(3-bromo-4-ethoxybenzoyl)benzimidazole,
1-diethylaminosulfonyl-2-amino-5(6)-(α-methoxyimino-3,4-dichlorobenzyl)benzimidazole,
1-(N-methyl-N-propylaminosulfonyl)-2-amino-5(6)-(α-hydroxyimino-3-bromo-4-ethoxybenzyl)benzimidazole,
1-(N-ethyl-N-propylaminosulfonyl)-2-amino-5(6)-(α-thiocarbamylhydrazono-3-methoxy-4-ethoxybenzyl)benzimidazole,
1-dimethylaminosulfonyl-2-amino-5(6)-(α-hydroxyimino-3-chloro-4-ethoxybenzyl)benzimidazole, and
1-(N-methyl-N-ethylaminosulfonyl)-2-amino-5(6)-(α-propoxyimino-2-iodo-4-butoxybenzyl)benzimidazole.

The sulfonylbenzimidazole compounds were tested as pure compounds and as isomer mixtures. Both isomers inhibit virus growth, the 6-isomer generally being more active than the 5-isomer.

Compounds coming within the scope of the above formula are able to suppress the growth of several viruses when added to a medium in which the virus is growing. The compounds of the invention can therefore be used in aqueous solution, preferably with a surfactant, to decontaminate surfaces on which polio, Coxsackie, rhinovirus or other viruses are present, such surfaces including hospital glassware and hospital working surfaces and similar areas in the preparation of food.

Furthermore, the compounds can be orally administered to warm-blooded mammals including humans in doses of 1 to 300 mg./kg. of mammalian body weight. The administration can be repeated periodically as needed. In accordance with general practice, the antiviral compound can be administered every 4 to 6 hours.

Preferably, the compounds to be employed in accordance with the present invention are employed in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, clacium sulfate, acacia powder, gelatin, sodium alginate, sodium benzoate and stearic acid. Such compositions can be formulated as tablets or enclosed in capsules for convenient administration. In addition, the compounds can be administered parenterally.

The compounds can also be mixed with a liquid and administered as nose drops or intranasal spray.

Illustrative of the esters, hydrazides and hydroxymethyl intermediates which can be used to prepare the compounds of the invention are the following:

ethyl 1-isopropanesulfonyl-2-amino-5(6)-benzimidazolecarboxylate,
ethyl 1-(2-acetamido-4-methylthiazol-5-yl)-sulfonyl-2-propionamido-5(6)-benzimidazolecarboxylate,
ethyl 1-(2-methylamino-1,3,4-thiadiazol-5-yl)-sulfonyl-2-amino-5(6)-benzimidazolecarboxylate,
ethyl 1-(N-methyl-N-propylaminosulfonyl)-2-formamido-5(6)-benzimidazolecarboxylate,
ethyl 1-piperidinosulfonyl-2-acetamido-5(6)-benzimidazolecarboxylate,
ethyl 1-(2-furan)sulfonyl-2-propionamido-5(6)-benzimidazolecarboxylate,
ethyl 1-(1,3,4-thiadiazol-5-yl)sulfonyl-2-amino-5(6)-benzimidazolecarboxylate,
ethyl 1-(N-methyl-N-ethylaminosulfonyl)-2-formamido-5(6)-benzimidazolecarboxylate,
ethyl 1-pyrrolidinosulfonyl-2-acetamido-5(6)-benzimidazolecarboxylate,
ethyl 1-butanesulfonyl-2-propionamido-5(6)-benzimidazolecarboxylate,
ethyl 1-cyclohexanesulfonyl-2-amino-5(6)-benzimidazolecarboxylate,
ethyl 1-(2-thiophene)sulfonyl-2-acetamido-5(6)-benzimidazolecarboxylate,
ethyl 1-(2-methyl-1,3,4-thiadiazol-5-yl)sulfonyl-2-propionamido-5(6)-benzimidazolecarboxylate,
ethyl 1-(N-ethyl-N-propylaminosulfonyl)-2-amino-5(6)-benzimidazolecarboxylate,
ethyl 1-morpholinosulfonyl-2-acetamido-5(6)-benzimidazolecarboxylate,
ethyl 1-isobutanesulfonyl-2-propionamido-5(6)-benzimidazolecarboxylate,
ethyl 1-(2-thiophene)sulfonyl-2-acetamido-5(6)-benzimidazolecarboxylate,
ethyl 1-dimethylaminosulfonyl-2-propionamido-5(6)-benzimidazolecarboxylate,
1-isopropanesulfonyl-2-amino-5(6)-benzimidazolecarboxylic acid hydrazide,
1-cyclobutanesulfonyl-2-acetamido-5(6-benzimidazolecarboxylic acid hydrazide,
1-benzenesulfonyl-2-propionamido-5(6)-benzimidazolecarboxylic acid hydrazide,
1-(2-thiazole)sulfonyl-2-amino-5(6)-benzimidazolecarboxylic acid hydrazide,
1-(2-acetamido-4-methylthiazol-5-yl)sulfonyl-2-acetamido-5(6)-benzimidazolecarboxylic acid hydrazide,
1-(N-methyl-N-propylaminosulfonyl)-2-propionamido-5(6)-benzimidazolecarboxylic acid hydrazide,
1-pyrrolidinosulfonyl-2-amino-5(6)-benzimidazolecarboxylic acid hydrazide,
1-(1,3,4-thiadiazol-2-yl)sulfonyl-2-acetamido-5(6-benzimidazolecarboxylic acid hydrazide,
1-(2-methyl-1,3,4-thiadiazol-5-yl)sulfonyl-2-propionamido-5(6)-benzimidazolecarboxylic acid hydrazide,
1-diisopropylaminosulfonyl-2-amino-5(6)-benzimidazolecarboxylic acid hydrazide,
1-(3-furan)sulfonyl-2-acetamido-5(6)-benzimidazolecarboxylic acid hydrazide,
1-piperidinosulfonyl-2-propionamido-5(6)-benzimidazolecarboxylic acid hydrazide,
1-diethylaminosulfonyl-2-amino-5(6)-benzimidazolecarboxylic acid hydrazide,
1-cyclopropanesulfonyl-2-acetamido-5(6)-benzimidazolecarboxylic acid hydrazide,
1-pentanesulfonyl-2-formamido-5(6)-benzimidazolecarboxylic acid hydrazide,
1-(3-thiophene)sulfonyl-2-acetamido-5(6)-benzimidazolecarboxylic acid hydrazide,
1-ethanesulfonyl-2-propionamido-5(6)-hydroxymethylbenzimidazole,
1-cyclopropanesulfonyl-2-amino-5(6)-hydroxymethylbenzimidazole,
1-benzenesulfonyl-2-formamido-5(6)-hydroxymethylbenzimidazole,
1-(2-furan)sulfonyl-2-acetamido-5(6)-hydroxymethylbenzimidazole,
1-(2-thiazole)sulfonyl-2-propionamido-5(6)-hydroxymethylbenzimidazole,
1-(2-acetamido-4-methylthiazol-5-yl)sulfonyl-2-amino-5(6)-hydroxymethylbenzimidazole,
1-(2-methylamino-1,3,4-thiadiazol-5-yl)sulfonyl-2-formamido-5(6)-hydroxymethylbenzimidazole,
1-(N-methyl-N-propylaminosulfonyl)-2-acetamido-5(6)-hydroxymethylbenzimidazole,
1-dipropylaminosulfonyl-2-propionamido-5(6)-hydroxymethylbenzimidazole,
1-pyrrolidinosulfonyl-2-amino-5(6)-hydroxymethylbenzimidazole,
1-morpholinosulfonyl-2-formamido-5(6)-hydroxymethylbenzimidazole,
1-isobutanesulfonyl-2-acetamido-5(6)-hydroxymethylbenzimidazole,
1-cyclopentanesulfonyl-2-propionamido-5(6)-hydroxymethylbenzimidazole, 1-(1,3,4-thiadiazol-2-yl)sulfonyl-2-amino-5(6)-hydroxymethylbenzimidazole,
1-(N-ethyl-N-propylaminosulfonyl)-2-formamido-5(6)-hydroxymethylbenzimidazole,
1-morpholinosulfonyl-2-acetamido-5(6)-hydroxymethylbenzimidazole,
1-benzenesulfonyl-2-propionamido-5(6)-hydroxymethylbenzimidazole,
1-(4-methylthiazol-5-yl)sulfonyl-2-amino-5(6)-hydroxymethylbenzimidazole,
1-cyclohexanesulfonyl-2-formamido-5(6)-hydroxymethylbenzimidazole,
1-diethylaminosulfonyl-2-acetamido-5(6)-hydroxymethylbenzimidazole,
1-cycloheptanesulfonyl-2-propionamido-5(6)-hydroxymethylbenzimidazole,
1-diethylaminosulfonyl-2-amino-5(6)-hydroxymethylbenzimidazole, and
1-(N-ethyl-N-isopropylaminosulfonyl)-2-formamido-5(6)-hydroxymethylbenzimidazole.

Illustrative of the 5(6)-formyl sulfonyl benzimidazole compounds and their derivatives provided by this invention are the following:
1-cyclohexanesulfonyl-2-formamido-5(6)-formylbenzimidazole,
1-[(2-acetamido-4-methylthiazol-2-yl)sulfonyl]-2-amino-5(6)-formylbenzimidazole,
1-diethylaminosulfonyl-2-acetamido-5(6)-formylbenzimidazole,
1-pyrrolidinosulfonyl-2-propionamido-5(6)-formylbenzimidazole,
1-cyclopentanesulfonyl-2-acetamido-5(6)-formylbenzimidazole,
1-morpholinosulfonyl-2-formamido-5(6)-formylbenzimidazole,
1-(2-thiophene)sulfonyl-2-propionamido-5(6)-formylbenzimidazole,
1-benzenesulfonyl-2-amino-5(6)-formylbenzimidazole,
1-(2-thiazole)sulfonyl-2-acetamido-5(6)-formylbenzimidazole,
1-piperidinosulfonyl-2-formamido-5(6)-formylbenzimidazole,
1-butanesulfonyl-2-amino-5(6)-formylbenzimidazole,
1-methanesulfonyl-2-acetamido-5(6)-formylbenzimidazole,
1-isopropanesulfonyl-2-propionamido-5(6)-formylbenzimidazole,
1-(2-thiophene)sulfonyl-2-amino-5(6)-formylbenzimidazole,
1-cyclopentanesulfonyl-2-acetamido-5(6)-formylbenzimidazole,
1-isopropanesulfonyl-2-amino-5(6)-formylbenzimidazole,
1-pentanesulfonyl-2-acetamido-5(6)-formylbenzimidazole,
1-ethanesulfonyl-2-formamido-5(6)-formylbenzimidazole,
1-(2-furan)sulfonyl-2-acetamido-5(6)-formylbenzimidazole,
1-benzenesulfonyl-2-propionamido-5(6)-formylbenzimidazole,
1-dipropylaminosulfonyl-2-acetamido-5(6)-formylbenzimidazole,
1-pyrrolidinosulfonyl-2-amino-5(6)-(hydrazonomethyl)benzimidazole,
1-piperidinosulfonyl-2-acetamido-5(6)-(1,3-dithiolan-2-yl)benzimidazole,
1-morpholinosulfonyl-2-formamido-5(6)-(1,3-dithian-2-yl)benzimidazole,
1-dimethylaminosulfonyl-2-propionamido-5(6)-(isopropoxyiminomethyl)benzimidazole,
1-cyclopropanesulfonyl-2-formamido-5(6)-(thiocarbamylhydrazonomethyl)benzimidazole,
1-(2-thiazole)sulfonyl-2-acetamido-5(6)-(1,3-dithiolan-2-yl)benzimidazole,
1-isopropanesulfonyl-2-amino-5(6)-(1,3-dithian-2-yl)benzimidazole,
1-dimethylaminosulfonyl-2-propionamido-5(6)-(methoxyiminomethyl)benzimidazole,
1-benzenesulfonyl-2-formamido-5(6)-(hydroxyiminomethyl)benzimidazole,
1-isopropanesulfonyl-2-amino-5(6)-(hydroxyiminomethyl)benzimidazole,
1-isopropanesulfonyl-2-acetamido-5(6)-(hydrazonomethyl)benzimidazole,
1-dimethylaminosulfonyl-2-amino-5(6)-(hydrazonomethyl)benzimidazole,
1-dimethylaminosulfonyl-2-acetamido-5(6)-(carbamylhydrazonomethyl)benzimidazole,
1-dimethylaminosulfonyl-2-amino-5(6)-(thiocarbamylhydrazonomethyl)benzimidazole,
1-dimethylaminosulfonyl-2-acetamido-5(6)-hydroxyiminomethyl)benzimidazole,
1-diethylaminosulfonyl-2-amino-5(6)-(methoxyiminomethyl)benzimidazole,
1-dipropylamino-2-acetamido-5(6)-(ethoxyiminomethyl)benzimidazole,
1-diisopropylaminosulfonyl-2-propionamido-5(6)-(propoxyiminomethyl)benzimidazole,
1-cyclobutanesulfonyl-2-amino-5(6)-(isopropoxyiminomethyl)benzimidazole,
1-dimethylaminosulfonyl-2-acetamido-5(6)-(butoxyiminomethyl)benzimidazole,
1-piperidinosulfonyl-2-formamido-5(6)-(isobutoxyiminomethyl)benzimidazole,
1-(2-thiophene)sulfonyl-2-acetamido-5(6)-(secbutoxyiminomethyl)benzimidazole,
1-(2-acetamido-4-methylthiazol-2-yl)sulfonyl-2-amino-5(6)-(tert-butoxyiminomethyl)benzimidazole,
1-dimethylaminosulfonyl-2-amino-5(6)-(1,3-dithiolan-2-yl)benzimidazole,
1-dimethylamino-2-acetamido-5(6)-(1,3-dithian-2-yl)benzimidazole,
1-isopropanesulfonyl-2-acetamido-5(6)-(1,3-dithiolan-2-yl)benzimidazole, and
1-cyclohexanesulfonyl-2-formamido-5(6)-(1,3-dithian-2-yl)benzimidazole.

Illustrative of the 5(6)-keto sulfonylbenzimidazole compounds and their derivatives provided by this invention are the following:
a compound wherein $R_3$ is $Z=C(R_6)-$, wherein $R_6$ is phenyl or phenyl substituted by chloro and Z is hydroxyimino,
a compound wherein $R_3$ is $Z=C(R_6)-$, wherein $R_6$ is phenyl and Z is $C_1-C_4$ alkoxyimino,
a compound wherein $R_3$ is $Z=C(R_6)-$, wherein $R_6$ is phenyl and Z is $C_1-C_4$ acyloxyimino,
a compound wherein $R_3$ is $Z=C(R_6)-$, wherein $R_6$ is phenyl or $C_1-C_7$ alkyl and Z is benzoyloxyimino, or thiocarbamylhydrazono.
1-isopropanesulfonyl-2-amino-5(6)-acetylbenzimidazole,
1-cyclopentanesulfonyl-2-acetamido-5(6)-propionylbenzimidazole, 1-cyclopropanesulfonyl-2-formamido-5(6)-isopropionylbenzimidazole,
1-dimethylaminosulfonyl-2-acetamido 5(6)-butyrylbenzimidazole,
1-piperidinosulfonyl-2-propionamido-5(6)-isobutyrylbenzimidazole,
1-diethylaminosulfonyl-2-amino-5(6)-pentanoylbenzimidazole,
1-dipropylaminosulfonyl-2-formamido-5(6)-hexanoylbenzimidazole,
1-pentanesulfonyl-2-amino-5(6)-heptanoylbenzimidazole,
1-(2-thiophene)sulfonyl-2-acetamido-5(6)-octanoylbenzimidazole,
1-dimethylaminosulfonyl-2-amino-5(6)-cyclopropylcarbonylbenzimidazole,
1-piperidinosulfonyl-2-propionamido-5(6)-isopentanoylbenzimidazole,
1-diethylaminosulfonyl-2-amino-5(6)-cyclopropylcarbonylbenzimidazole,
1-(2-thiophene)sulfonyl-2-acetamido-5(6)-cyclobutylcarbonylbenzimidazole,
1-(2-thiazole)sulfonyl-2-formamido-5(6)-cyclopentylcarbonylbenzimidazole,
1-(2-acetamido-4-methylthiazol-2-yl)sulfonyl-2-propionamido-5(6)-cyclohexylcarbonylbenzimidazole,
1-(5-methyl-1,3,4-thiadiazol-2-yl)sulfonyl-2-formamido-5(6)-cycloheptylcarbonylbenzimidazole,
1-(3-furan)sulfonyl-2-amino-5(6)-(1-hydrazonoethyl)benzimidazole,
1-cyclohexanesulfonyl-2-acetamido-5(6)-(1-hydroxyiminopropyl)benzimidazole,
1-isopropanesulfonyl-2-propionamido-5(6)-(1-methoxyiminoisopropyl)benzimidazole,
1-dimethylaminosulfonyl-2-amino-5(6)-(1-ethoxyiminobutyl)benzimidazole,
1-piperidinosulfonyl-2-propionamido-5(6)-(1-propoxyiminoisobutyl)benzimidazole,
1-(5-methylamino-1,3,4-thiadiazol-2-yl)sulfonyl-2-amino-5(6)-(1-isopropoxyiminopentyl)benzimidazole,
1-benzenesulfonyl-2-acetamido-5(6)-(1-butoxyiminohexyl)benzimidazole,
1-cyclopropanesulfonyl-2-formamido-5(6)-(1-carbamylhydrazonoheptyl)benzimidazole,
1-(3-thiophene)sulfonyl-2-acetamido-5(6)-(1-thiocarbamylhydrazonoethyl)benzimidazole,
1-dimethylaminosulfonyl-2-amino-5(6)-(α-hydrazonocyclopentylmethyl)benzimidazole,
1-cyclobutanesulfonyl-2-acetamido-5(6)-(α-hydroxyiminocyclobutylmethyl)benzimidazole,
1-(2-furan)sulfonyl-2-formamido-5(6)-(α-methoxyiminocyclopentylmethyl)benzimidazole,
1-diethylaminosulfonyl-2-propionamido-5(6)-(α-ethoxyiminocyclohexylmethyl)benzimidazole,
1-morpholinosulfonyl-2-amino-5(6)-(α-propoxyiminocyclopentylmethyl)benzimidazole,
1-(2-thiazole)sulfonyl-2-acetamido-5(6)-(1-isopropoxyiminoisobutyl)benzimidazole,
1-(5-methylamino-1,3,4-thiadiazol-2-yl)sulfonyl-2-formamido-5(6)-(1-butoxyiminoisopropyl)benzimidazole,
1-dimethylaminosulfonyl-2-amino-5(6)-[α-(thiocarbamylhydrazono)cyclopentylmethyl]benzimidazole,
1-diisopropylaminosulfonyl-2-acetamido-5(6)[α-(carbamylhydrazono)cyclobutylmethyl]benzimidazole,
1-pyrrolidinosulfonyl-2-propionamido-5(6)-(1-hydroxyiminoisoamyl)benzimidazole,
1-butanesulfonyl-2-formamido-5(6)-(1-hydrazonooctyl)benzimidazole,
1-dimethylaminosulfonyl-2-amino-5(6)-(1-hydrazonopropyl)benzimidazole,
1-(2-acetamido-4-methylthiazol-2-yl)sulfonyl-2-amino-5(6)-[(α-methoxyimino)cyclopropylmethyl]benzimidazole,
1-cycloheptanesulfonyl-2-formamido-5(6)-(1-carbamylhydrazonoethyl)benzimidazole,
1-(2-thiophene)sulfonyl-2-propionamido-5(6)-(1-thiocarbamylhydrazonoethyl)benzimidazole,
1-dimethylaminosulfonyl-2-acetamido-5(6)-[α-butoxyimino(cycloheptylethyl]benzimidazole,
1-pyrrolidinosulfonyl-2-amino-5(6)-(1-hydroxyiminopropyl]benzimidazole,
1-dimethylaminosulfonyl-2-amino-5(6)-[(α-ethoxyimino)cyclohexylmethyl]benzimidazole,
1-dimethylaminosulfonyl-2-amino-5(6)-cyclopropylacetylbenzimidazole,
1-isopropanesulfonyl-2-acetamido-5(6)-cyclobutylacetylbenzimidazole,
1-methanesulfonyl-2-formamido-5(6)-cyclopentylacetylbenzimidazole,
1-(2-thiophene)sulfonyl-2-methyl-5(6)-cyclohexylacetylbenzimidazole,
1-piperidinosulfonyl-2-amino-5(6)-cycloheptyl-acetylbenzimidazole,
1-dimethylaminosulfonyl-2-amino-5(6)-[(1-hydrazono2-cyclopropyl)ethyl]benzimidazole,
1-isopropanesulfonyl-2-propionamido-5(6)-[(1-hydroxyimino-2-cyclobutyl)ethyl]benzimidazole,
1-benzenesulfonyl-2-amino-5(6)-[(1-methoxyimino-2-cyclopentyl)ethyl]benzimidazole,
1-[(2-furan)sulfonyl]-2-amino-5(6)-[(1-ethoxyimino-2-cyclohexyl)ethyl]benzimidazole,
1-piperidinosulfonyl-2-formamido-5(6)-[(1-propoxyimino-2-cycloheptyl)ethyl]benzimidazole,
1-[(5-methyl-1,3,4-thiadiazol-5-yl)sulfonyl]-2-amino-5(6)-[(1-isopropoxy-2-cyclopropyl)ethyl]benzimidazole,
1-pyrrolidinosulfonyl-2-propionamido-5(6)-[(1-butoxyimino-2-cyclobutyl)ethyl]benzimidazole
1dimethylaminosulfonyl-2-amino-5(6)-[(1-carbamylhydrazono-2-cyclopropyl)ethyl]benzimidazole,
1-morpholinosulfonyl-2-amino-5(6)-[(1-thiocarbamylhydrazono-2-cyclopentyl)ethyl]benzimidazole,
1-dimethylaminosulfonyl-2-propionamido-5(6)-(2-cyclopropylpropionyl)benzimidazole,
1-isopropanesulfonyl-2-amino-5(6)-(2-cyclobutylpropionyl)benzimidazole,
1-benzenesulfonyl-2-acetamido-5(6)-(2-cyclopentylpropionyl)benzimidazole,
1-(3-furan)sulfonyl-2-amino-5(6)-(2-cyclohexylpropionyl)benzimidazole,
1-(5-methylamino-1,3,4-thiadiazol-5-yl)sulfonyl-2-amino-5(6)-(2-cycloheptylpropionyl)benzimidazole,
1-dimethylaminosulfonyl-2-amino-5(6)-[(1-hydrazono-2-cyclopropyl)propyl]benzimidazole,
1-isopropanesulfonyl-2-acetamido-5(6)-[(1-hydroxyimino-2-cyclobutyl)propyl]benzimidazole,
1-(2-acetamido-4-methylthiazol-2-yl)sulfonyl-2-formamido-5(6)-[(1-methoxyimino-2-cyclopentyl)propyl]benzimidazole,
1-piperidinosulfonyl-2-amino-5(6)-[(1-ethoxyimino-2-cyclohexyl)propyl]benzimidazole,
1-benzenesulfonyl-2-propionamido-5(6)-[(1-propoxyimino-2-cycloheptyl)propyl]benzimidazole, 1-butanesulfonyl-2-amino-5(6)-[(1-butoxyimino-2-cyclopropyl)propyl]benzimidazole,
1-[(2-thiazole)sulfonyl]-2-acetamido-5(6)-[(1-carbamylhydrazono-2-cyclopropyl)propyl]benzimidazole,
1-dimethylaminosulfonyl-2-amino-5(6)-[(1-thiocarbamylhydrazono-2-cyclopentyl)propyl]benzimidazole,
1-pyrrolidinosulfonyl-2-propionamido-5(6)-[(1-carbamylhydrazono-2-cyclohexyl)propyl]benzimidazole,
1-dimethylaminosulfonyl-2-amino-5(6)-(n-pentanoyloxyiminobenzyl)benzimidazole,
1-dimethylaminosulfonyl-2-amino-5(6)-(pivaloyloxyiminobenzyl)benzimidazole,
1-dimethylaminosulfonyl-2-amino-5(6)-(3-methoxycarbonylpropionyloxyiminobenzyl)benzimidazole,
1-dimethylaminosulfonyl-2-amino-5(6)-[2-(p-nitrobenzyloxycarbonyl)-ethylcarbonyloxyiminobenzyl]benzimidazole,
1-dimethylaminosulfonyl-2-amino-5(6)-(benzyloxycarbonylaminomethylcarbonyloxyiminobenzyl)benzimidazole,
1-dimethylaminosulfonyl-2-amino-5(6)-(phthalimidomethylcarbonyloxyiminobenzyl)benzimidazole,
1-dimethylaminosulfonyl-2-amino-5(6)-[2-(2-benzyloxycarbonyl-5-oxoisoxazolidin-4-yl)ethylcarbonyloxyiminobenzyl]benzimidazole,
1-isopropylsulfonyl-2-amino-6-[α-(3-pentylidene)benzyl]benzimidazole,
1-isopropylsulfonyl-2-amino-6-(α-isopropylidenebenzyl)benzimidazole,
1-isopropylsulfonyl-2-amino-6-(α-isopropyl-α-hydroxybenzyl)benzimidazole, and
1-dimethylaminosulfonyl-2-amino-6-[α-(3-pentylidene)benzyl]benzimidazole.

Illustrative of the 5(6)-heterocyclic sulfonylbenzimidazole compounds provided by this invention are the following:
1-isopropanesulfonyl-2-amino-5(6)-(1,3,4-oxadiazol-2-yl)benzimidazole,
1-cyclopentanesulfonyl-2-formamido-5(6)-(2-methyl-1,3,4-oxodiazol-5-yl)benzimidazole,
1-benzenesulfonyl-2-acetamido-5(6)-(2-ethyl-1,3,4-oxadiazol-5-yl)benzimidazole,
1-(2-furan)sulfonyl-2-propionamido-5(6)-(2-propyl-1,3,4-oxadiazol-5-yl)benzimidazole,
1-(2-methyl-1,3,4-thiadiazol-5-yl)sulfonyl-2-amino-5(6)-(2-butyl-1,3,4-oxadiazol-5-)benzimidazole,
1-(2-acetamido-4-methylthiazol-5-yl)sulfonyl-2-formamido-5(6)-(1,3,4-oxadiazol-2-yl)benzimidazole,
1-diethylaminosulfonyl-2-acetamido-5(6)-(2-methyl-1,3,4-oxadiazol-5-yl)benzimidazole,
1-(N-methyl-N-isopropylaminosulfonyl)-2-propionamido-5(6)-(2-propyl-1,3,4-oxadiazol-5-yl)benzimidazole,
1-piperidinosulfonyl-2-amino-5(6)-(2-butyl-1,3,4-oxadiazol-5-yl)benzimidazole,
1-butanesulfonyl-2-formamido-5(6)-(1,3,4-oxadiazol-2-yl)benzimidazole,
1-cyclopropanesulfonyl-2-acetamido-5(6)-(2-methyl-1,3,4-oxadiazol-5-yl)benzimidazole,
1-ethanesulfonyl-2-amino-5(6)-(tetrazol-5-yl)-benzimidazole,
1-cyclobutanesulfonyl-2-formamido-5(6)-[1(2)-methyltetrazol-5-yl]benzimidazole,
1-benzenesulfonyl-2-acetamido-5(6)-[1(2)-propyltetrazol-5-yl]benzimidazole,
1-(2-thiophene)sulfonyl-2-propionamido-5(6)-[1(2)-butyltetrazol-5-yl] benzimidazole,
1-(2-acetamido-4-methyltetrazol-5-yl)sulfonyl-2-amino-5(6)-(tetrazol-5-yl)benzimidazole,
1-(2-acetamido-4-methyltetrazol-5-yl)sulfonyl-2-amino-5(6)-(tetrazol-5-yl)benzimidazole,
1-(2-methyl-1,3,4-thiadiazol-5-yl)sulfonyl-2-formamido-5(6)-[1(2)-methyltetrazol-5-yl] benzimidazole,
1-diisopropylaminosulfonyl-2-acetamido-5(6)-[1(2)-ethyltetrazol-5-yl] benzimidazole,
1-(N-ethyl-N-propylaminosulfonyl)-2-propionamido-5(6)-[1(2)-propyltetrazol-5-yl] benzimidazole,
1-pyrrolidinosulfonyl-2-amino-5(6)-[1(2)-butyltetrazol-5-yl] benzimidazole,
1-morpholinosulfonyl-2-formamido-5(6)-(tetrazol-5-yl)benzimidazole,
1-isopropanesulfonyl-2-acetamido-5(6)-[1(2)-methyltetrazol-5-yl] benzimidazole,
1-cyclopropanesulfonyl-2-propionamido-5(6)-[1(2)-ethyltetrazol-5-yl] benzimidazole,
1-cycloheptanesulfonyl-2-amino-5(6)-[1(2)-propyltetrazol-5-yl] benzimidazole, and
1-(2-thiazole)sulfonyl-2-formamido-5(6)-[1(2)-butyltetrazol-5-yl] benzimidazole.

Illustrative of the 5(6)-hydroxy sulfonylbenzimidazole compounds and the esters derived therefrom provided by this invention are the following:
1-ethanesulfonyl-2-amino-5(6)-hydroxybenzimidazole,
1-isopropanesulfonyl-2-formamido-5(6)-hydroxybenzimidazole,
1-pentanesulfonyl-2-acetamido-5(6)-hydroxybenzimidazole,
1-cyclobutanesulfonyl-2-propionamido-5(6)-hydroxybenzimidazole,
1-cyclohexanesulfonyl-2-amino-5(6)-hydroxybenzimidazole,
1-benzenesulfonyl-2-formamido-5(6)-hydroxybenzimidazole,
1-(3-furan)sulfonyl-2-acetamido-5(6)-hydroxybenzimidazole,
1-(2-thiophene)sulfonyl-2-propionamido-5(6)-hydroxybenzimidazole,
1-(2-acetamido-4-methylthiazol-5-yl)-2-amino-5(6)-hydroxybenzimidazole,
1-(2-methylamino-1,3,4-thiadiazol-5-yl)sulfonyl-2-formamido-5(6)-hydroxybenzimidazole,
1-diisopropylaminosulfonyl-2-acetamido-5(6)-hydroxybenzimidazole,
1-(N-methyl-N-isopropylaminosulfonyl)-2-propionamido-5(6)-hydroxybenzimidazole,
1-piperidinosulfonyl-2-amino-5(6)-hydroxybenzimidazole,
1-morpholinosulfonyl-2-formamido-5(6)-hydroxybenzimidazole,
1-dimethylaminosulfonyl-2-amino-5(6)-propionyloxybenzimidazole,
1-isopropanesulfonyl-2-acetamido-5(6)-phenylacetoxybenzimidazole,
1-cyclopropanesulfonyl-2-formamido-5(6)-benzoyloxybenzimidazole,
1-benzenesulfonyl-2-propionamido-5(6)-pentanoyloxybenzimidazole,
1-(3-furan)sulfonyl-2-amino-5(6)-phenylacetoxybenzimidazole, 1-(2-acetamido-4-methylthiazol-5-yl)sulfonyl-2-amino-5(6)-benzoyloxybenzimidazole,
1-piperidinosulfonyl-2-formamido-5(6)-heptanoyloxybenzimidazole,
1-cyclopentanesulfonyl-2-propionamido-5(6)-acetoxybenzimidazole,
1-dimethylaminosulfonyl-2-amino-5(6)-phenylacetoxybenzimidazole,
1-dimethylamino-2-amino-5(6)-benzoyloxybenzimidazole,
1-(2-acetamido-4-methylthiazol-5-yl)sulfonyl-2-acetamido-5(6)-octanoyloxybenzimidazole,
1-pyrrolidinosulfonyl-2-formamido-5(6)-phenylacetoxybenzimidazole,
1-cyclobutanesulfonyl-2-amino-5(6)-benzoyloxybenzimidazole,
1-(2-thiophene)sulfonyl-2-acetamido-5(6)-propionyloxybenzimidazole,
1-dimethylaminosulfonyl-2-amino-5(6)-octanoyloxybenzimidazole, The following examples further illustrate the preparation of the starting materials, intermediates, and compounds of the invention. The term "m/e" used in characterizing the products refers to the mass-to-charge ratio of ions which appear in the mass spectra of the products. In general, the values correspond to molecular weights of the major peaks.

EXAMPLE 1

Ethyl 1-dimethylaminosulfonyl-2-amino-6-benzimidazolecarboxylate.

One hundred and forty grams (0.68 mole) of ethyl 2-amino-5(6)-benzimidazolecarboxylate was stirred in 500 ml. of acetone and 77 ml. of triethylamine. One hundred grams of dimethylsulfamoyl chloride dissolved in 100 ml. of acetone was added through a dropping funnel to the stirred reaction mixture. The reaction mixture was refluxed for about 100 hours. The hot mixture was filtered to yield solid A. The filtrate was allowed to cool and solid B crystallized out overnight. Solids A and B were combined and washed with water to remove triethylamine hydrochloride. The product was dissolved in about 1.5 l of hot 2B ethanol. The hot ethanol solution was filtered to separate insoluble material. The ethanol filtrate was allowed to cool whereupon product crystallized. The product was collected to give 23 g. of ethyl 1-dimethylaminosulfonyl-2-amino-6-benzimidazolecarboxylate, mp. 215°–217° C.

Analysis: $C_{12}H_{16}N_4O_4S$ MW 312 Calcd: C, 46.14; H, 5.16; N, 17.94 Found: C, 45.87; H, 5.05; N, 18.21

The ethanol filtrate was evaporated in vacuo to a small volume to yield 15 g. of the 5-isomer, ethyl 1-dimethylaminosulfonyl-2-amino-5-benzimidazolecarboxylate, mp. 167°–168° C. The 5-isomer was characterized by nmr and elemental analysis. The total yield of product was 38 g. (18 percent).

Examples 2–10
The following Ethyl 1-(Substituted-Sulfonyl)-2-Amino-5(6)-Benzimidazolecarboxylates were prepared by the method of Example 1.

| | | | Analysis (Percent) | | | | | |
|---|---|---|---|---|---|---|---|---|
| | | MP | Theory | | | Found | | |
| No. | Sulfonyl Substituent | °C | C | H | N | C | H | N |
| 2 | isopropyl* | 166–168 | 50.15 | 5.50 | 13.50 | 49.86 | 5.48 | 13.24 |
| 3 | isopropyl** | 165–167 | 50.15 | 5.50 | 13.50 | 49.92 | 5.26 | 13.44 |
| 4 | benzene | | 55.64 | 4.38 | 12.17 | 55.86 | 4.48 | 12.22 |
| 5 | (N-methyl-N-ethylamino) | | 47.84 | 5.56 | f 17.17 | 48.09 | 5.49 | 16.97 |
| 6 | diethylamino | 142–143 | 49.40 | 5.92 | 16.46 | 49.73 | 5.90 | 16.18 |
| 7 | (N-methyl-N-propyl-amino) | 140–148 | 49.40 | 5.92 | 16.46 | 49.30 | 6.13 | 16.37 |
| 8 | 2-thiophene | | 47.85 | 3.73 | 11.96 | 47.67 | 3.84 | 11.76 |
| 9 | (2-acetamido-4-methyl-thiazol-5-yl) | | 45.39 | 4.02 | 16.54 | 45.52 | 4.43 | 15.94 |
| 10 | (2-methylamino-1,3,4-thiadiazol-5-yl) | | 40.83 | 3.69 | 21.98 | 40.59 | 3.94 | 21.78 |

*5-isomer, **6-isomer, other esters are 5(6)-isomeric mixtures.
The esters of Example 1–10 can be chemically reduced by the the method of Example 11 to provide the corresponding 5(6)-hydroxymethyl sulfonylbenzimidazole compounds.

EXAMPLE 11

1-Dimethylaminosulfonyl-2-amino-5(6)-hydroxymethylbenzimidazole (A) 2-Amino-5(6)-hydroxymethylbenzimidazole Twenty-four and six-tenths grams of ethyl 2-amino-5(6)-benzimidazolecarboxylate was suspended in 600 ml. of tetrahydrofuran (THF) under nitrogen. Ninety-six ml. (0.36 mole) of sodium bis(2-methoxyethoxy)-aluminum hydride (RED-AL) in 400 ml. of THF was added dropwise to the stirred reaction mixture at a rate such that the temperature did not exceed 35° C. The mixture was heated at reflux for about 20 hours. The excess RED-AL was decomposed by the addition of 30 ml. of water. The mixture was filtered and the filtrate was evaporated to dryness in vacuo. The foamy residue was treated with 150 ml. of ethyl acetate and 200 ml. of water. The aqueous emulsified phase was separated. The aqueous phase was filtered to yield a yellow solid. The aqueous filtrate was evaporated in vacuo to yield a second crop. The combined yield was 12.3 g. (65 percent) of crude 2-amino-5(6)-hydroxymethylbenzimidazole. An analytical sample of the isomeric mixture was prepared.

Analysis: $C_8H_9N_3O$ MW 163 Calcd.: C, 58.88; H, 5.56; N, 25.75 Found: C, 58.65; H, 5.48; N, 25.54

(B) 1-Dimethylaminosulfonyl-2-amino-5(6)-hydroxymethylbenzimidazole

Thirty millimoles, 4.9 g., of 2-amino-5(6)-hydroxymethylbenzimidazole were dissolved in 40 ml. of acetone and thirty millimoles, 3.03 g., of triethylamine. To the acetone solution were added 4.32 g. (30 mmoles) of dimethylsulfamoyl chloride. The mixture was heated at reflux for about 17 hours. The mixture was poured in 25 ml. of water. The aqueous mixture was extracted with chloroform. The chloroform extract was washed successively with water and saturated sodium chloride solution. The chloroform solution was filtered and dried. The chloroform was evaporated to dryness in vacuo, to yield 5.5 g. (66 percent) of crude product as an isomeric mixture.

Seven grams of crude isomeric mixture were chromatographed over Woelm silica gel using ethyl acetate as the eluant. The 6-isomer was collected after 6 l. of eluant had passed over the column. The yield was 1.02 g. of 1-dimethylaminosulfonyl-2-amino-6-hydroxymethylbenzimidazole, mp. 182°–183° C. (ethyl acetate-methanol)

Analysis: $C_{10}H_{14}N_4O_3S$ MW 270 Calcd.: C, 44.43; H, 5.22; N, 20.73 Found: C, 44.37; H, 5.18; N, 20.44

EXAMPLE 12

2-Amino-5(6)-hydroxymethylbenzimidazole (A) 4-Amino-3-nitrobenzyl alcohol

Fifty grams (0.27 mole) of 4-chloro-3-nitrobenzyl alcohol, 250 ml. of methanol and 200 ml. of liquid ammonia were loaded into a cold autoclave. The autoclave was sealed and heated to a temperature of 150° C. The reaction was continued for 6 hours. After cooling the autoclave was vented and the reaction mixture was evaporated in vacuo. The residue was taken up in ether and the ether solution was filtered to separate the ammonium chloride. The ether filtrate was evaporated in vacuo to yield a solid product. The product was recrystallized from 2-B ethanol/ethyl acetate to give 23.6 g. (52 percent yield) of 4-amino-3-nitrobenzyl alcohol, mp. 100°–101° C.

Analysis: $C_7H_8N_2O_3$ MW 168 Calcd: C, 50.00; H, 4.80; N, 16.66. Found: C, 49.72; H, 4.56; N, 16.44.

(B) 3,4-Diaminobenzyl alcohol

Six grams (0.035 mole) of 4-amino-3-nitrobenzyl alcohol, 95 ml. of tetrahydrofuran and 0.5 g. of Raney Nickel were hydrogenated at 40 psi at room temperature until 3 moles of hydrogen were absorbed. The catalyst was filtered and the filtrate was evaporated in vacuo to yield 4.83 g. (82 percent yield) of 3,4-diaminobenzyl alcohol, mp. 74°–75° C.

Analysis: $C_7H_{10}N_2O$ MW 138 Calcd: C, 60.85; H, 7.30; N, 20.28. Found: C, 60.90; H, 7.15; N, 19.99.

(C) 2-Amino-5(6)-hydroxymethylbenzimidazole.

Two grams (0.014 mole) of 3,4-diaminobenzyl alcohol were dissolved in 40 ml. of methanol. To this solution was added a solution of 1.6 g. (0.014 mole) of cyanogen bromide in 10 ml. of methanol. After standing overnight at room temperature, the reaction mixture was evaporated to dryness in vacuo to give 3.4 g. (97 percent yield) of the hydrobromide salt of 2-amino-5(6)-hydroxymethylbenzimidazole.

Alternatively, this product may also be obtained from 4-amino-3-nitrobenzyl alcohol without isolation of the intermediate diamine after hydrogenation. The filtrate obtained after removal of the hydrogenation catalyst was treated with a solution of cyanogen bromide in methanol. The product was isolated as described above.

EXAMPLE 13

1-Dimethylaminosulfonyl-2-amino-5(6)-formylbenzimidazole

Two hundred and fifty miligrams of 1-dimethylaminosulfonyl-2-amino-5(6)-hydroxymethylbenzimidazole were suspended in 7 ml. of acetone and the mixture was cooled in an ice bath. Jones reagent (0.3 ml.) was added to the cold reaction mixture and the reaction was continued at 0° C. for about 5 minutes. The mixture was poured into 40 ml. of water. The aqueous mixture was extracted with chloroform (40 ml. portions). The chloroform extract was washed with water and saturated sodium chloride solution and dried. The chloroform was evaporated in vacuo to leave a solid residue. The residue was recrystallized from ethyl acetate to yield 57 mg. (1st crop) of 1-dimethylaminosulfonyl-2-amino-5(6)-formylbenzimidazole.

Analysis $C_{10}H_{12}N_4O_3S$ MW 268 Calcd: C, 44.71; H, 4.51; N, 20.88 Found: C, 44.75; H, 4.52; N, 20.63

EXAMPLE 14

1-Dimethylaminosulfonyl-2-amino-5(6)-(hydroxyiminomethyl)benzimidazole

One millimole, 268 mg. of 1-dimethylaminosulfonyl-2-amino-5(6)-formylbenzimidazole, 101 mg. (1 mmole) of triethylamine, 69 mg. (1 mmole) of hydroxylamine hydrochloride and 5 drops of water were heated under reflux for about 20 hours. The cooled reaction mixture was filtered to give 140 mg. of the oxime product. The filtrate was poured in 30 ml. of water. The aqueous mixture was extracted with ethyl acetate. The organic phase was washed with water and dried (MgSO$_4$). The ethyl acetate was evaporated in vacuo to give an additional 87 mg. of the oxime product.

Analysis $C_{10}H_{13}N_5O_3S$ MW 263 Calcd: C, 42.55; H, 4.28; N, 24.81. Found: C,42.03; H, 4.31; N, 23.91.

EXAMPLE 15

1-Dimethylaminosulfonyl-2-amino-5(6)-(hydrazonomethyl)benzimidazole

One millimole, 268 mg., of 1-dimethylaminosulfonyl-2-amino-5(6)-formylbenzimidazole, 20 ml. of methanol, and 32 mg. of hydrazine were heated at reflux for about 16 hours. The reaction mixture was evaporated in vacuo to about one-fourth the original volume. The mixture was poured into 30 ml. of water. The precipitated product was collected to give 80 mg. of the hydrazone product. The aqueous filtrate was evaporated to dryness in vacuo to give an additional 75 mg. of the hydrazone derivative. $m/e$ 282.

EXAMPLE 16

1-Dimethylaminosulfonyl-2-amino-5(6)-thiocarbamylhydrazonomethylbenzimidazole

Two hundred and fifty milligrams of 1-dimethylaminosulfonyl-2-amino-5(6)-formylbenzimidazole, 15 ml. of methanol, and 70 mg. of thiosemicarbazide was heated at reflux for about 3 hours. The thiosemicarbazone product precipitated upon cooling and was collected to give 170 mg. of solid. The thiosemicarbazone was recrystallized from a mixture of methanol (6 ml.) and chloroform (2 ml.) to yield 100 mg. of 1-dimethylaminosulfonyl-2-amino-5(6)-thiocarbamylhydrazonomethylbenzimidazole.

Analysis $C_{11}H_{15}N_7O_2S_2$ MW 341 Calcd: C, 38.70; H, 4.43; N, 28.72 Found: C, 38.87; H, 4.64; N, 28.57

EXAMPLE 17

1-Dimethylaminosulfonyl-2-amino-5(6)-carbamylhydrazonomethylbenzimidazole

Two millimoles, 536 mg., of 1-dimethylaminosulfonyl-2-amino-5(6)-formylbenzimidazole, 4 ml. of methanol, 222 mg. of semicarbazide, and 0.5 ml. of water were heated under reflux for about 2 hours. Two milliliters of methanol were added to the cooled reaction mixture and the precipitated product was collected. The product was washed with cold methanol to yield 226 mg. of the semicarbazone product. The combined filtrates were evaporated in vacuo to a small volume. The residue was treated with 50 ml. of saturated sodium chloride solution. The aqueous solution was extracted with methylene chloride. The extract was washed with water and saturated sodium chloride solution and dried. The methylene chloride was evaporated to dryness in vacuo to give a second crop, 160 mg., of 1-dimethylaminosulfonyl-2-amino-5(6)-carbamylhydrazonomethylbenzimidazole. m/e 325.

EXAMPLE 18

1-Dimethylaminosulfonyl-2-amino-5(6)-(1,3-dithiolan-2-yl)benzimidazole

One millimole, 268 mg., of 1-dimethylaminosulfonyl-2-amino-5(6)-formylbenzimidazole, 5 ml. of methanol, 0.2 ml. of ethanedithiol and 0.2 ml. of boron trifluoride etherate were reacted at room temperature for about 2 hours. The product precipitated out of solution and was filtered. The solid product was washed with cold methanol to give 65 mg. of the cyclic thioacetal, 1-dimethylaminosulfonyl-2-amino-5(6)-(dithiolan-2-yl)benzimidazole. The washings and filtrates were combined and mixed with 20 ml. of saturated sodium carbonate solution. The aqueous solution was extracted with ethyl acetate. The extract was washed with saturated sodium chloride solution and dried ($MgSO_4$). The ethyl acetate was evaporated to dryness in vacuo. The solid residue was reated with methanol and the methanol insoluble material was collected, yield 155 mg. of 1-dimethylaminosulfonyl-2-amino-5(6)-(1,3-dithiolan-2-yl)benzimidazole. The methanol filtrate was evaporated to dryness in vacuo to give 95 mg. of additional product. m/e 344.

EXAMPLE 19

1-Dimethylaminosulfonyl-2-amino-5(6)-(1,3-dithian-2yl)benzimidazole

Two hundred and twenty milligrams (0.8 mmole) of 1-dimethylaminosulfonyl-2-amino-5(6)-formylbenzimidazole, 2 ml. of methanol, 0.15 ml. (1.6 mmole) of 1,3-propanedithiol, and 0.75 ml. of boron trifluoride etherate were reacted at room temperature. About 6 ml. of ether was added to the mixture which was allowed to react for about 2 hours. The reaction mixture was diluted to a volume of 12 ml. with ether and product precipitated out of solution. The mixture was centrifuged and the supernatant liquid was decanted. The precipitate was suspended in ether and the mixture was again centrifuged. The supernatant liquid was decanted and the solid product was dried under vacuum to yield 224 mg. (75 percent) of the cyclic thioacetal product, 1-dimethylaminosulfonyl-2-amino-5(6)-(1,3-dithian-2-yl)benzimidazole. m/e 358.

EXAMPLE 20

1-Dimethylaminosulfonyl-2-amino-5(6)-methoxyiminomethylbenzimidazole

A solution of 135 mg. of 1-dimethylaminosulfonyl-2-amino-5(6)-formylbenzimidazole and methoxyamine hydrochloride in 20 ml. of methanol was refluxed for 17 hours. The color of the solution changed from red to yellow. The reaction mixture was concentrated to one-half its volume and then 9 ml. of a buffer solution (pH = 7.00) was added. The mixture was concentrated by evaporation, filtered, washed with water and dried to yield 42 mg. of 1-dimethylaminosulfonyl-2-amino-5(6)-methoxyiminomethylbenzimidazole. m/e 297.

EXAMPLE 21

1-Dimethylaminosulfonyl-2-amino-5(6)-acetylbenzimidazole (A) 4-Acetamidoacetophenone One hundred grams of p-aminoacetophenone was added portionwise to 400 ml. of acetic anhydride. Pyridine was added to maintain a homogeneous solution. The reaction mixture was stirred for 2 hours at room temperature. The mixture was poured into 3.5 l. of cold water. The precipitated product was collected to yield 108.5 g. (93 percent) of 4-acetamidoacetophenone.

Analysis $C_{10}H_{11}NO_2$ MW 177 Calcd: C, 67.78; H, 6.26; N, 7.90 Found: C, 68.03; H, 6.47; N, 8.02

(B) 3-Nitro-4-acetamidoacetophenone

Five grams of 4-acetamidoacetophenone were added portionwise to 25 ml. of red fuming nitric acid at 0°–5° C. After the addition was completed the mixture was stirred for about 15 minutes. The reaction mixture was carefully poured over ice. The precipitated product was collected to yield 4.7 g. (75 percent) of 3-nitro-4-acetamidoacetophenone.

(C) 3-Nitro-4-aminoacetophenone

Sixteen grams of 3-nitro-4-acetamidoacetophenone in 160 ml. of concentrated sulfuric acid were stirred at room temperature for about one hour. The mixture was carefully poured into cold water and the precipitated product was filtered to yield 9.5 g. (73 percent) of 3-nitro-4-aminoacetophenone.

Analysis $C_8H_8N_2O_3$ MW 180 Calcd: C, 53.33; H, 4.48; N, 15.55 Found: C, 53,18; H, 4.33; N, 15.87.

(D) 2-Amino-5(6)-acetylbenzimidazole

Four and one-half grams of 3-nitro-4-aminoacetophenone were hydrogenated at 60 psi in 145 ml. of ethyl acetate with 1 g. of platinum oxide and 3 g. of Raney nickel at room temperature. Three equivalents of hydrogen were absorbed in 5 hours. The catalyst was filtered. Three grams of cyanogen bromide was added to the filtrate and the mixture was stirred for about 24 hours. The hydrobromide salt of the product precipitated and was collected to yield 2 g. of 2-amino-5(6)-acetylbenzimidazole hydrobromide.

Analysis $C_9H_9N_3O \cdot HBr$ MW 256 Calcd: C, 42.21; H, 3.94; N, 16.41 Found: C, 42.43; H, 4.09; N, 16.35

(E)
1-Dimethylaminosulfonyl-2-amino-5(6)-acetylbenzimidazole

Four grams (15.6 mmole) of 2-amino-5(6)-acetylbenzimidazole hydrobromide, 50 ml. of acetone, 5 ml. (35.6 mmole) of triethylamine and 2.3 g. (16.0 mmole) of dimethylsulfamoyl chloride were refluxed for about 12 hours. The mixture was filtered and the filtrate was evaporated in vacuo to a solid residue. The residue was taken up in 80 ml. of methanol. The methanol solution was concentrated to about 60 ml. and cooled. The product crystallized to yield 800 mg. of 1-dimethylaminosulfonyl-2-amino-5(6)-acetylbenzimidazole, yellow crystals, mp. 206°–210° C. (dec).

Analysis $C_{11}H_{14}N_4O_3S$ MW 282 Calcd: C, 46.80; H, 5.00; N, 19.85 Found: C, 47.07; H, 4.99; N, 19.65.

EXAMPLE 22

1-Dimethylaminosulfonyl-2-amino 5(6)-propionylbenzimidazole (A) Beginning with p-aminopropionphenone according to Example 20, ten grams (0.053 mole) of 2-amino-5(6)-propionylbenzimidazole, 100 ml. of acetone, 10 ml. of triethylamine and 8.6 g. of dimethylsulfamoyl chloride were reacted to yield the crude product. Recrystallization from 600 ml. of methanol gave about 6.0 g. of the 5-isomer, 1-dimethylaminosulfonyl-2-amino-5-propionylbenzimidazole, mp. 206°–208° C.

Analysis $C_{12}H_{18}N_4O_3S$ MW 296 Calcd: C, 48.64; H, 5.44; N, 18.91 Found: C, 48.41; H, 5.49; N, 18.73

(B) There was obtained 2.8 g. of methanol insoluble material from the crystallization above which proved to be the 6-isomer, 1-dimethylaminosulfonyl-2-amino-6-propionylbenzimidazole, confirmed by NMR.

Analysis $C_{12}H_{18}N_4O_3S$ MW 296 Calcd: C, 48.64; H, 5.44; N, 18.91 Found: C, 48.58; H, 5.63; N, 18.71

EXAMPLE 23

1-Dimethylaminosulfonyl-2-amino-5(6)-butyrylbenzimidazole

When 5.7 g. of 2-amino-5(6)-butyrylbenzimidazole, 30 ml. of acetone, 5.7 g. of triethylamine 4.0 g. of dimethylsulfamoyl chloride were substituted in the procedure of Example 21, there was obtained 292 mg. of 1-dimethylaminosulfonyl-2-amino-5(6)-butyrylbenzimidazole.

Analysis: $C_{13}H_{18}N_4O_3S$ MW 310 Calcd: C, 50.31; H, 5.05; N, 18.05 Found: C, 49.93; H, 5.73; N, 17.84

EXAMPLE 24

1-Dimethylaminosulfonyl-2-amino-5(6)-(α-hydroxyiminoethyl)benzimidazole

A solution of 423 mg. of 1-dimethylaminosulfonyl-2-amino-5(6)-acetylbenzimidazole and 300 mg. of hydroxylamine hydrochloride in 60 ml. of methanol was refluxed for 17 hours. The solution was concentrated on a steam bath to one-half its volume. To the solution was added 30 ml. of buffer solution (pH = 7.00). A precipitate formed which was filtered and dried to yield 318 mg. of 1-dimethylaminosulfonyl-2-amino-5(6)-(α-hydroxyiminoethyl)benzimidazole. mp. 222°–225° C. (dec)

Analysis: $C_{11}H_{15}N_5O_3S$ MW 297 Calcd: C, 44.43; H, 5.09; N, 23.55 Found: C, 44.64; H, 4.96; N, 23.21

EXAMPLE 25

1-Dimethylaminosulfonyl-2-amino-5(6)-(α-methoxyiminoethyl)benzimidazole

A solution of 141 mg. (0.5 mmole) of 1-dimethylaminosulfonyl-2-amino-5(6)-acetylbenzimidazole and 120 mg. (1.45 mmoles) of methoxyamine hydrochloride in 20 ml. of methanol was refluxed for 19 hours. The solution was concentrated on a steam bath to one-half its volume, then an equal volume of water was added. The solution was then concentrated until a solid started to appear. To the solution was added 5 ml. of buffer solution (pH = 7.00) which resulted in more crystallization. The solution was filtered, washed twice with water and dried to yield 75 mg. of 1-dimethylaminosulfonyl-2-amino-5(6)-(α-methoxyiminoethyl)benzimidazole, mp. 183°–185° C.

Analysis: $C_{12}H_{17}N_5O_3S$ MW 311 Calcd: C, 46.29; H, 5.50; N, 22.49 Found: C, 46.50; H, 5.43; N, 22.22

EXAMPLE 26

1-Dimethylaminosulfonyl-2-amino-5(6)-(α-thiocarbamylhydrazonoethyl)benzimidazole Four hundred and twenty-three mg. of 1-dimethylaminosulfonyl-2-amino-5(6)-acetylbenzimidazole, 300 mg. of thiosemicarbazide, and 1.5 ml. of 1N hydrochloric acid in 60 ml. of methanol was refluxed for 16.5 hours. The solution was concentrated on a steam bath and 30 ml. of buffer solution (pH = 7.00) added. The product precipitated, filtered and dried to yield 360 mg. of 1-dimethylaminosulfonyl-2-amino-5(6)-(α-thiocarbamylhydrazonoethyl)benzimidazole, mp. 230°–235° C. (dec)

Analysis: $C_{12}H_{17}N_7O_2S_2$ MW 355 Calcd: C, 40.55; H, 4.82; N, 27.59 Found: C, 40.22; H, 4.50; N, 27.27

EXAMPLE 27

1-Dimethylaminosulfonyl-2-amino-5(6)-(α-thiocarbamylhydrazonopropyl)benzimidazole One hundred forty eight mg. (0.5 mmoles) of 1-dimethylaminosulfonyl-2-amino-5(6)-propionylbenzimidazole, 100 mg. (1 mmole) of thiosemicarbazide, 20 ml. of methanol and 0.5 ml. of 1N hydrochloric acid was refluxed with stirring for 17.5 hours. The solution was concentrated to one-half its volume on a steam bath, an equal volume of water was added, and the solution was allowed to cool. On standing the product precipitated to yield 53 mg. of 1-dimethylaminosulfonyl-2-amino-5(6)-(α-thiocarbamylhydrazonopropyl)-benzimidazole. m/e 369.

EXAMPLE 28

1-Dimethylaminosulfonyl-2-formamido-5(6)-propionylbenzimidazole

Ten ml. of acetic anhydride were cooled to 0° C. in an ice bath. Five ml. of 97–100 percent formic acid was slowly added. The solution was warmed to 55° C. on a steam bath for 15 minutes, then cooled quickly and 1 g. (0.0035 mole) of 1-dimethylaminosulfonyl-2-amino-5(6)-propionylbenzimidazole was added. The slurry was cooled in an ice bath for 2 hours. The solution was poured onto 50 g. of ice, filtered, washed with water, and dried to yield 1.1 g. of 1-dimethylaminosulfonyl-2-formamido-5(6)-propionylbenzimidazole.

Analysis: $C_{13}H_{16}N_4O_4S$ MW 324 Calcd: C, 48.14; H, 4.97; N, 17.27 Found: C, 48.37; H, 5.12; N, 17.05

EXAMPLE 29

1-Dimethylaminosulfonyl-2-amino-6-benzoylbenzimidazole

(A) 2-Amino-5(6)-benzoylbenzimidazole

Three-hundred grams (1.52 mole) of 4-aminobenzophenone were added in portions to a stirred solution of 250 ml. of acetic anhydride in 250 ml. of benzene. The temperature of the mixture rose to about 70° C. The reaction mixture was stirred overnight. The preciptated product was filtered, washed with benzene and dried. The yield of 4-acetamidobenzophenone was 333.8 g. (91.5 percent yield), mp. 150°–152° C. (Lit. mp. 155° C., Chem. Abst. 55, 18651).

Twenty-three grams (0.1 mole) of 4-acetamidobenzophenone, 50 ml. of acetic anhydride and 20 ml. of acetic acid were stirred together. A solution of 90 percent nitric acid (15 ml.), 10 ml. of acetic acid and 0.2 g. of urea was added dropwise to the benzophenone mixture. The reaction mixture was maintained at a temperature of about 50° C. during the nitration. The mixture was stirred at ambient temperature whereupon the mixture became very thick. The thick slurry was poured over ice and the insoluble product was filtered to yield 17.7 g. (62.5 percent yield) of 4-acetamido-3-nitrobenzophenone.

Analysis: $C_{15}N_2O_4$ MW 284.27 Calcd: C, 63.38; H, 4.26; N, 9.85; O, 22.51. Found: C, 63.57; H, 4.03; N, 9.90; O, 22.27.

Ten grams of 4-acetamido-3-nitrobenzophenone were added portionwise to 40 ml. of sulfuric acid. The reaction temperature was moderated with a water bath. After stirring about 45 minutes the reaction mixture was carefully poured over ice. The precipitated product was filtered to yield 4-amino-3-nitrobenzophenone.

Analysis: $C_{13}H_{10}N_2O_3$ MW 242.23 Calcd: C, 64.46; H, 4.16; N, 11.56; O, 19.81. Found: C, 64.19; H, 4.00; N, 11.37; O, 19.72.

Fifty grams of 4-amino-3-nitrobenzophenone were hydrogenated at room temperature in 945 ml. of tetrahydrofuran with 15 g. of Raney nickel at $2.74 \times 10^6$ dynes/cm.$^2$. After 4 hours three equivalents of hydrogen were absorbed. The catalyst was filtered and the filtrate was evaporated in vacuo to a solid residue. The residue was chromatographed over silica gel using ethyl acetate as eluant. Fractions 5–9 were combined to yield 43.6 g. (100 percent yield) of 3,4-diaminobenzopheone.

Two-tenths mole, 42.4 g., of 3,4-diaminobenzophenone were dissolved in 100 ml. of methanol and mixed into one liter of water. Two-tenths mole, 21.8 g, of cyanogen bromide were added in portions to the reaction mixture with stirring. The reaction was continued overnight. The reaction mixture was filtered and the filtrate was neutralized (pH 7.0) with concentrated ammonium hydroxide. The precipitated product was collected, washed with water, and dried in a vacuum oven to yield 31 g. (68.5 percent) of 2-amino-5(6)-benzoylbenzimidazole.

Analysis: $C_{14}H_{11}N_3O$ MW 237.2 Calcd: C, 70.87; H, 4.67; N, 17.71. Found: C, 70.88; H, 4.60; N, 17.48.

(B) 1-Dimethylaminosulfonyl-2-amino-5(6)-benzoylbenzimidazole

Twenty millimoles, 4.5 g., of 2-amino-5(6)-benzoylbenzimidazole were dissolved in 30 ml. of acetone and 4.0 g. of triethylamine. A solution of 2.9 g. (20 mmole) of dimethylsulfamoyl chloride in 10 ml. of acetone was added dropwise to the reaction mixture. The mixture was heated at reflux overnight. The reaction mixture was poured into 400 ml. of water. The product was extracted with chloroform. The extract was washed with water, dried ($Na_2SO_4$) and evaporated in vacuo to a residue. The residue was crystallized from ethyl acetate to yield 1.06 g. of 1-dimethylaminosulfonyl-2-amino-6-benzoylbenzimidazole, mp. 206°–208° C.

Analysis: $C_{16}H_{16}N_4O_3S$ MW 344 Calcd: C, 55.82; H, 4.65; N, 16.28. Found: C, 56.27; H, 4.80; N, 15.95.

EXAMPLE 30

1-Isopropylsulfonyl-2-amino-6-benzoylbenzimidazole

Thirty g. (0.126 mole) of 2-amino-5(6)-benzoylbenzimidazole, 250 ml. of dimethoxyethane, and 6.3 g. (0.13 mole) of sodium hydride (50 percent in mineral oil) were stirred for one hour. To the mixture was added 19 g. of isopropylsulfonyl chloride in 20 ml. of dimethoxyethane. The mixture was stirred 16 hours at room temperature, refluxed for 2 hours, cooled, concentrated under vacuum, dissolved in 1500 ml. of ethyl acetate, washed with water, dried, and concentrated by boiling to 200 ml. When the solution cooled a precipitate formed which was filtered, and washed with diethyl ether to yield 11.1 g. of 1-isopropylsulfonyl-2-amino-6-benzoylbenzimidazole.

Analysis: $C_{17}H_{17}N_3O_3S$ MW 343 Calcd: C, 59.46; H, 4.99; N, 12.24 Found: C, 59.20; H, 5.03; N, 12.03

EXAMPLE 31

1-Dimethylaminosulfonyl-2-formamido-5(6)-benzoylbenzimidazole

Ten ml. of acetic anhydride was added to 5 ml. of 97–100 percent formic acid. The solution was stirred and heated to 50°–55° C. for 15 minutes, then cooled to 0° C. in an ice bath. To the solution was added 1.0 g. of 1-dimethylaminosulfonyl-2-amino-5(6)-benzoylbenzimidazole and stirred for 2 hours. The solution was then poured over ice, extracted twice with chloroform, washed the extracts once with water and once with saturated sodium chloride, filtered and evaporated to yield 900 mg. of oil. The oil was then dissolved in methanol and dried to yield 800 mg. of 1-dimethylaminosulfonyl-2-formamido-5(6)-benzoylbenzimidazole. m/e 372.

EXAMPLE 32

1-Dimethylaminosulfonyl-2-acetamido-5(6)-benzoylbenzimidazole

A mixture of 1.0 g. of 1-dimethylaminosulfonyl-2-amino-5(6)-benzoylbenzimidazole, 4 ml. of acetic anhydride and 400 mg. of anhydrous sodium acetate were heated to 50° C. for 10 minutes. The mixture was stirred, 60 ml. of water was added, and the mixture stood for 16 hours. The solution was extracted three times with chloroform, washed three times with water, washed once with saturated sodium chloride and dried to give 1.0 g. of 1-dimethylaminosulfonyl-2-acetamido-5(6)-benzoylbenzimidazole. m/e 386.

EXAMPLE 33

1-Dimethylaminosulfonyl-2-amino-5(6)-p-chlorobenzoylbenzimidazole

When the procedure of Example 30 was repeated using 1.1 g. of 2-amino-5(6)-p-chlorobenzoylbenzimidazole and 576 mg. of dimethylsulfamoyl chloride as starting materials, there was obtained 1-dimethylaminosulfonyl-2-amino-5(6)-p-chlorobenzoylbenzimidazole. m/e 378.

EXAMPLE 34

1-Dimethylaminosulfonyl-2-amino-5(6)-($\alpha$-hydroxyiminobenzyl)benzimidazole One hundred seventy two milligrams of 1-dimethylaminosulfonyl-2-amino-5(6)-benzoylbenzimidazole, 100 mg. of hydroxylamine hydrochloride and 20 ml. of methanol were refluxed for 16 hours. The reaction mixture was concentrated to one-half the original volume by heating on the steam bath. Ten milliliters of buffer (pH=7.0) were added to the mixture. The product precipitated and was filtered to yield 116 mg. of 1-dimethylaminosulfonyl-2-amino-5(6)-($\alpha$-hydroxyiminobenzyl)benzimidazole, mp. 180°–183° C.

Analysis: $C_{16}H_{17}N_5O_3S$ MW 359 Calcd: C, 53,47; H, 4.77: N, 19.49. Found: C, 53.42; H, 4.60; N, 19.17

EXAMPLE 35

1-Isopropylsulfonyl-2-amino-5(6)-($\alpha$-hydroxyiminobenzyl)benzimidazole

A mixture of 1.7 g. (0.005 mole) of 1-isopropylsulfonyl-2-amino-5(6)-benzoylbenzimidazole, 1 g. of hydroxylamine hydrochloride, and 200 ml. of methanol were refluxed for 18 hours. The reaction mixture was concentrated to one-half the original volume by heating on the steam bath. One hundred ml. of bufffer (pH=7.0) were added to the mixture and the mixture was allowed to cool. The product precipitated and was filtered to yield 1.2 g. of 1-isopropylsulfonyl-2-amino-5(6)-($\alpha$-hydroxyiminobenzyl)benzimidazole. m/e 358.

Analysis: $C_{17}H_{18}N_4O_3S$ MW 358 Calcd: C, 56.97; H, 5.06; N, 15.63 Found: C, 56.67; H, 5.34; N, 15.25

EXAMPLE 36

1-Dimethylaminosulfonyl-2-amino-5(6)-($\alpha$-hydroxyimino-p-chlorobenzyl)benzimidazole When 1.1 g. (3 mmoles) of 1-dimethylaminosulfonyl-2-amino-5(6)-p-chlorobenzoylbenzimidazole, 600 mg. of hydroxylamine hydrochloride and 120 ml. of methanol are substituted in the procedure of Example 34, there was obtained 1.5 g. of 1-dimethylaminosulfonyl-2-amino-5(6)-($\alpha$-hydroxyimino-p-chlorobenzyl)benzimidazole. m/e 378.

EXAMPLE 37

1-Dimethylaminosulfonyl-2-amino-5(6)-($\alpha$-methoxyiminobenzyl)benzimidazole When 688 mg. (2 mmole) of 1-dimethylaminosulfonyl-2-amino-5(6)-benzoylbenzimidazole, 500 mg. of methoxyamine hydrochloride and 80 ml. of methanol were substituted in the procedure of Example 25, there was obtained 530 mg. of 1-dimethylaminosulfonyl-2-amino-5(6)-($\alpha$-methoxyiminobenzyl)benzimidazole.

Analysis: $C_{17}H_{19}N_5O_3S$ MW 373. Calcd: C, 54.68; H, 5.13; N, 18.75. Found: C, 54.66; H, 5.06; N, 18.92.

EXAMPLE 38

1-Isopropylsulfonyl-2-amino-5(6)-($\alpha$-methoxyiminobenzyl)benzimidazole

When 1.7 g. of 1-isopropylsulfonyl-2-amino-5(6)-benzoylbenzimidazole, 1.2 g. of methoxyamine hydrochloride, and 200 ml. of methanol were substituted in the procedure of Example 25, there was obtained an oil. The oil was treated with a saturated solution of sodium chloride, extracted with ethyl acetate and dried. After extraction several times with benzene there was obtained 1 g. of 1-isopropylsulfonyl2-amino-5(6)-($\alpha$-methoxyiminobenzyl)benzimidazole, as a solid foam.

Analysis: $C_{18}H_{20}N_4O_3S$ MW 372. Calcd: C, 58.05; H, 5.41; N, 15.04. Found: C, 57.98; H, 5.72; N, 14.99.

EXAMPLE 39

1-Dimethylaminosulfonyl-2-amino-5(6)-($\alpha$-ethoxyiminobenzyl)benzimidazole To 15 ml. of absolute ethanol was added 718 mg. (2 mmole) of 1-dimethylaminosulfonyl-2-amino-5(6)-($\alpha$-hydroxyiminobenzyl)benzimidazole with stirring. To the solution was added 120 mg. (2.2 mmole) of sodium methoxide, then 552 mg. (3.54 mmole) of ethyl iodide. The solution was refluxed for 2½ hours, cooled, and evaporated to one-half the volumn. The solution was poured into water, extracted twice with chloroform, washed twice with saturated sodium chloride, dried and filtered to yield 227 mg., as a white foamy solid, 1-dimethylaminosulfonyl-2-amino-5(6)-($\alpha$-ethoxyiminobenzyl)benzimidazole.

Analysis: $C_{18}H_{21}N_5O_3S$ MW 387. Calcd: C, 55.80; H, 5.46; N, 18.08. Found: C, 56.03; H, 5.33; N, 18.27.

EXAMPLE 40

1-Dimethylaminosulfonyl-2-amino-5(6)-($\alpha$-propoxyiminobenzyl)benzimidazole When 718 mg. (2 mmole) of 1-dimethylaminosulfonyl-2-amino-5(6)-($\alpha$-hydroxyiminobenzyl)benzimidazole, 15 ml. of methanol, 120 mg. (2.2 mmoles) of sodium methoxide and 600 mg. (3.54 mmole) of 1-iodopropane were substituted in the procedure of Example 39, there was obtained 248 mg. of 1-dimethylaminosulfonyl-2-amino-5(6)-($\alpha$-propoxyiminobenzyl)-benzimidazole, as a white solid.

Analysis: $C_{19}H_{23}N_5O_3S$ MW 401 Calcd: C, 56.84; H, 5.77; N, 17.44 Found: C, 56.63; H, 5.54; N, 17.60

EXAMPLE 41

1-Dimethylaminosulfonyl-2-amino-5(6)-($\alpha$-benzyloxyiminobenzyl)benzimidazole A solution of 172 mg. (0.5 mmole) of 1-dimethylaminosulfonyl-2-amino-5(6)-benzoylbenzimidazole, 230 mg. (1.45 mmoles) of benzyloxyamine hydrochloride and 20 ml. of methanol was refluxed for 19½ hours. The solution was then treated according to the procedure of Example 34 to yield 161 mg. of 1-dimethylaminosulfonyl-2-amino-5(6)-($\alpha$-benzyloxyiminobenzyl)benzimidazole.

Analysis: $C_{23}H_{23}N_5O_3S$ MW 449 Calcd: C, 61.45; H, 5.16; N, 15.58 Found: C, 61.51; H, 5.20; N, 15.37

EXAMPLE 42
1-Dimethylaminosulfonyl-2-amino-5(6)-(α-acetoxyiminobenzyl)benzimidazole To a solution of 359 mg. (1 mmole) of 1-dimethylaminosulfonyl-2-amino-5(6)-(α-hydroxyiminobenzyl)benzimidazole in 4.4 ml. of dimethylformamide was added 54 mg. (1 mmole) of sodium methoxide with stirring. One hundred and two mg. (1 mmole) of acetic anhydride was added to the solution and the solution stirred for 5 minutes. To the solution was added 26.5 ml. of water and 25 ml. of buffer (pH=7.00). The solution was stirred one hour, then filtered to yield 320 mg. of 1-dimethylaminosulfonyl-2-amino-5(6)-(α-acetoxyiminobenzyl)benzimidazole. mp. 137°-139° C.

Analysis: $C_{18}H_{19}N_5O_4S$ MW 401. Calcd: C, 53.85; H, 4.77; N, 17.45. Found: C, 53.58; H, 4.59; N, 17.80.

EXAMPLE 43
1-Isopropylsulfonyl-2-amino-5(6)-(α-acetoxyiminobenzyl)benzimidazole When 1 g. (0.003 mole) of 1-isopropylsulfonyl2-amino-5(6)-(α-hydroxyiminobenzyl)benzimidazole, 162 mg. (0.003 mole) of sodium methoxide, 10 ml. of dimethylformamide, and 0.3 ml. of acetic anhydride were substituted in the procedure of Example 40, there was obtained 900 mg. of 1-isopropylsulfonyl-2-amino-5(6)-(α-acetoxyiminobenzyl)benzimidazole.

Analysis: $C_{19}H_{20}N_4O_4S$ MW 400. Calcd: C, 56.99; H, 5.03; N, 13.99. Found: C, 57.20; H, 5.24; N, 13.86.

EXAMPLE 44
1-Dimethylaminosulfonyl-2-acetamido-5(6)-(α-acetoxyiminobenzyl)benzimidazole One hundred and eighty-one mg. of 1-dimethylaminosulfonyl-2-amino-5(6)-(α-hydroxyiminobenzyl)benzimidazole, 2 ml. of pyridine, and 2 ml. of acetic anhydride were mixed and allowed to stand at room temperature for 17½ hours. The solution was then evaporated to dryness, extracted with methanol, and evaporated to yield 132 mg. of 1-dimethylaminosulfonyl-2-acetamido-5(6)-(α-acetoxyiminobenzyl)benzimidazole. mp. 162°-165° C. (dec)

Analysis: $C_{29}H_{21}N_5O_5S$ MW 443. Calcd: C, 54.17; H, 4.77; N, 15.79. Found: C, 54.03; H, 4.89; N, 15.85.

EXAMPLE 45
1-Dimethylaminosulfonyl-2-amino-5(6)-(α-propionyloxyiminobenzyl)benzimidazole When 359 mg. (1 mmole) of 1-dimethylaminosulfonyl2-amino-5(6)-(α-hydroxyiminobenzyl)benzimidazole, 4.4 ml. of dimethylformamide, 54 mg. (1 mmole) of sodium methoxide, and 130 mg. of propionic anhydride were substituted in the procedure of Example 42, there was obtained 367 mg. of 1-dimethylaminosulfonyl-2-amino-5(6)-(α-propionyloxyiminobenzyl)benzimidazole. m/e 415.

EXAMPLE 46
1-Dimethylaminosulfonyl-2-amino-5(6)-(α-butyryloxyiminobenzyl)benzimidazole When 359 mg. (1 mmole) of 1-dimethylaminosulfonyl2-amino-5(6)-(α-hydroxyiminobenzyl)benzimidazole, 4.4 ml. of dimethylformamide, 54 mg. of sodium methoxide, and 158 mg. (1 mmole) of butyric anhydride were substituted in the procedure of Example 42, there was obtained 342 mg. of 1-dimethylaminosulfonyl-2-amino-5(6)-(α-butyryloxyiminobenzyl)benzimidazole.

Analysis: $C_{20}H_{23}N_5O_4S$ MW 429 Calcd: C, 55.93; H, 5.40; N, 16.31 Found: C, 54.05; H, 5.21; N, 17.13

EXAMPLE 47
1-Dimethylaminosulfonyl-2-amino-5(6)-(α-benzoyloxyiminobenzyl)benzimidazole When 539 mg. (1.5 mmole) of 1-dimethylaminosulfonyl-2-amino-5(6)-(α-hydroxyiminobenzyl)benzimidazole, 6.6 ml. of dimethylformamide, 81 mg. (15 mmole) of sodium methoxide and 339 mg. (1.5 mmole) of benzoic anhydride were substituted in the procedure of Example 42, there was obtained 600 mg. of 1-dimethylaminosulfonyl-2-amino-5(6)-(α-benzoyloxyiminobenzyl)benzimidazole. m/e 463.

EXAMPLE 48
1-Dimethylaminosulfonyl-2-amino-5(6)-(α-methoxycarbonyloxyiminobenzyl)benzimidazole To a solution of 359 mg. (1 mmole) of 1-dimethylaminosulfonyl-2-amino-5(6)-(α-hydroxyiminobenzyl)benzimidazole in 4 ml. of dimethylformamide was added 63 mg. (1.2 mmole) of sodium methoxide. A solution of 100 mg. (1.1 mmole) of methoxycarbonyl chloride in 0.5 ml. of dimethylformamide was added to the reaction mixture. The mixture was stirred for 5 minutes, then 40 ml. of buffer (pH=7.00) was added. The mixture was stirred again for 5 minutes, filtered, washed with water, and dried to yield 290 mg. of 1-dimethylaminosulfonyl-2-amino-5(6)-(α-methoxycarbonyloxyiminobenzyl)benzimidazole. m/e 417.

EXAMPLE 49
1-Dimethylaminosulfonyl-2-amino-5(6)-thiocarbamylhydrazonobenzylbenzimidazole One hundred and seventy-two mg. of 1-dimethylaminosulfonyl-2-amino-5(6)-benzoylbenzimidazole, 100 mg. of thiosemicarbazide, and 0.5 ml. 1N hydrochloric acid in 20 ml. of methanol were refluxed for 16 hours. The thiosemicarbazone product precipitated upon cooling and was collected to yield 94 mg. of 1-dimethylaminosulfonyl-2-amino5(6)-thiocarbamylhydrazonobenzylbenzimidazole. m/e 417.

EXAMPLE 50
1-Dimethylaminosulfonyl-2-amino-5(6)-(α-ethoxycarbonylhydrazonobenzyl)benzimidazole To 300 ml. of boiling ethanol were added 3.2 g. (0.0093 mole) of 1-dimethylaminosulfonyl-2-amino-5(6)-benzoylbenzimidazole and 1 g. (0.0096 mole) of ethoxycarbonylhydrazine. The mixture was heated on a steam bath for 4 hours. One ml. of concentrated hydrochloric acid was added to the mixture, and then the mixture was heated for 10 hours. The solvent was removed under vacuum, 300 ml. of water was added. The solution stood 19 hours, was extracted with ethyl acetate, dried, and concentrated under vacuum to yield 1.7 g. of 1-dimethylaminosulfonyl-2-amino-5(6)-(α-ethoxycarbonylhydrazonobenzyl)benzimidazole, as a foam.

Analysis: $C_{19}H_{22}N_6O_4S$ MW 430. Calcd: C, 53.01; H, 5.15; N, 19.52. Found: C, 52.82; H, 5.51; N, 18.44.

EXAMPLE 51

1-Isopropylsulfonyl-2-amino-5(6)-(α-ethoxycarbonyl-hydrazonobenzyl)benzimidazole When the procedure of Example 50 was repeated using 3 g. (0.00875 mole) of 1-isopropylsulfonyl-2-amino5(6)-benzoylbenzimidazole, 300 ml. of absolute ethanol, 1 g. (0.0096 mole) of ethoxycarbonylhydrazine, and 1 ml. (0.01 mole) of concentrated hydrochloric acid, there was obtained 2.4 g. of 1-isopropylsulfonyl-2-amino-5(6)-(α-ethoxycarbonylhydrazonobenzyl)benzimidazole. m/e 429, 357, 343.

Analysis: $C_{20}H_{23}N_5O_4S$ MW 429. Calcd: C, 55.93; H, 5.40; N, 16.31. Found: C, 55.96; H, 5.10; N, 16.57.

EXAMPLE 52

1-Isopropylsulfonyl-2-amino-5(6)-(α-carboxymethoxyiminobenzyl)benzimidazole

When the procedure of Example 50 was repeated using 1.7 g. (0.005 mole) of 1-isopropylsulfonyl-2-amino5(6)-benzoylbenzimidazole, 200 ml. of methanol, 1.1 g. of carboxymethoxyamine hemihydrochloride, and 0.3 ml. (0.003 mole) of concentrated hydrochloric acid, there was obtained 2 g. of 1-isopropylsulfonyl-2-amino-5(6)-(α-carboxymethoxyiminobenzyl)benzimidazole. $pK_a$ 6.91 in 66 percent dimethylformamide/water.

EXAMPLE 53

1-Dimethylaminosulfonyl-2-amino-5(6)-[1(2)-methyltetrazol-5-yl]benzimidazole (A) 5-(3-Nitro-4-acetamidophenyl)tetrazole A solution of 10.3 g. (0.05 mole) of 3-nitro4-acetamidobenzonitrile, 3.5 g. of sodium azide and 3.9 g. of ammonium chloride 100 ml. of dimethylformamide was refluxed for 16 hours. The cooled reaction mixture was poured into 500 ml. of 1N hydrochloric acid and diluted with 300 ml. of water. The yellow product precipitated and was collected to yield 10 g. (81 percent) of 5-(3-nitro-4-acetamidophenyl)tetrazole. mp. 210°–213° C. (dec)

(B) 1(2)-Methyl-5-(3-nitro-4-acetamidophenyl)tetrazole 5-(3-Nitro-4-acetamidophenyl)tetrazole, 31.7 g. (0.13 mole), was dissolved in 200 ml. of acetone. Twenty three milliliters (0.17 mole) of triethylamine was added to the reaction mixture. The mixture was stirred until it became homogeneous. Thirty milliliters of methyl iodide were added followed by the addition of another 20 ml. of methyl iodide after 12 hours at room temperature. The reaction was continued another 4 hours. The precipitated product was collected and the filtrate was concentrated to one fourth the original volume in vacuo. The total yield was 20 g. (59 percent) of an isomeric mixture of 1(2)-methyl-5-(3-nitro-4-acetamidophenyl)tetrazole.

Analysis: $C_{10}H_{10}N_6O_3$ MW 262. Calcd: C, 45.80; H, 3.84; N, 32.05. Found: C, 45.64; H, 3.84; N, 32.18.

(C) 1(2)-Methyl-5-(3-nitro-4-aminophenyl)tetrazole

Two grams of 1(2)-methyl-5-(3-nitro-4-acetamidophenyl)tetrazole were added to 20 ml. of concentrated sulfuric acid at room temperature. The tetrazole slowly went into solution and the mixture was stirred for about 2 hours. The acid mixture was poured carefully into 200 ml. of cold water. The precipitated product was collected to yield 1.6 g. (95 percent) of 1(2)-methyl-5-(3-nitro4-amino)tetrazole, mp. about 200° C.

Analysis: $C_8H_8N_6O_2$ MW 220. Calcd: C, 43,64; H, 3.66; N, 38.17. Found: C, 43.37; H, 3.70; N, 37.89.

(D) 1(2)-Methyl-5-(3,4-diaminophenyl)tetrazole

Fourteen grams of 1(2)-methyl-5-(3-nitro-4-aminophenyl)tetrazole were hydrogenated at $4.13 \times 10^6$ dynes/cm.² with 1 g. of palladium-on-carbon in 135 ml. of ethyl acetate and 350 ml. of absolute ethanol. After 2 hours three equivalents of hydrogen were absorbed. The catalyst was filtered and the filtrate was evaporated in vacuo to yield 12 g. (98 percent) of 1(2)-methyl-5-(3,4-diaminophenyl)tetrazole.

Analysis: $C_8H_{10}N_6$ MW 190. Calcd: C, 50.52; H, 5.30; N, 44.18. Found: C, 50.79; H, 5.57; N, 43.95.

(E) 1(2)-Methyl-5-(2-aminobenzimidazol-5(6)-yl)tetrazole

Cyanogen bromide, 3.2 g. (0.03 mole), was added to a slurry of 5.7 g. (0.03 mole) of 1(2)-methyl-5-(3,4-diaminophenyl)tetrazole in 300 ml. of water and 30 ml. of methanol. The mixture was stirred for 12 hours and filtered. The filtrate was neutralized with potassium carbonate. The precipitated product was collected to yield 5.7 g. (88 percent) of 1(2)-methyl-5-(2-aminobenzimidazol-5(6)-yl)tetrazole.

Analysis: $C_9H_9N_7$ MW 215. Calcd: C, 50.23; H, 4.22; N, 45.56. Found: C, 49,56; H, 4.34; N, 44.06.

(F) 1-Dimethylaminosulfonyl-2-amino-5(6)-[1(2)Methyltetrazol-5-yl]benzimidazole

1(2)-Methyl-5-(2-aminobenzimidazol-5(6)-yl)tetrazole, 2.2 g. (0.01 mole), 50 ml. of acetone, 1.5 ml. of triethylamine, and 1 g. of dimethylsulfamoyl chloride were refluxed for 18 hours. After cooling unreacted starting material was filtered and the filtrate was evaporated to a residue in vacuo. The red oily residue was triturated with methanol to yield 300 mg. of 1-dimethylaminosulfonyl-2-amino-5(6)-[1(2)-methyltetrazol-5-yl]benzimidazole.

Analysis: $C_{11}H_{14}N_8O_2S$ MW 322 Calcd: C, 40.99; H, 4.38; N, 34.76 Found: C, 40.72; H, 4.38; N, 34.51.

The following intermediates and final product were prepared by the methods of Example 53. Alkylation of the tetrazole moiety with isopropyl iodide gave only a single isomer.

EXAMPLE 54

(A) 1-Isopropyl-5-(3-nitro-4-aminophenyl)tetrazole, mp. 126-128° C., yield 71 percent.

Analysis: $C_{10}H_{12}N_6O_2$ MW 200. Calcd: C, 48.38; H, 4.87; N, 33.85. Found: C, 48.19; H, 4.93; N, 33.61.

(B) 1-Isopropyl-5(3,4-diaminophenyl)tetrazole, yield 70 percent.

Analysis: $C_{10}H_{14}N_6$ MW 218. Calcd: C, 55.03; H, 6.47; N, 38.50. Found: C, 55.23; H, 6.27; N, 38.73.

(C)

1-Isopropyl-5-[2-aminobenzimidazol-5(6)-yl]tetrazole, mp. 232°–233° C., yield 7.3 g. (86 percent)

Analysis: $C_{11}H_{13}N_7$ MW 243 Calcd: C, 54.31; H, 5.39; N, 40.30 Found: C, 54.56; H, 5.54; N, 40.53

(D)

1-Dimethylaminosulfonyl-2-amino-5(6)-(1-isoproyltetrazol-5-yl)benzimidazole, mp. 211°-213° C.

Analysis: $C_{13}H_{18}N_8O_2S$ MW 350. Calcd: C, 44.56; H, 5.18; N, 31.98. Found: C, 44.83; H, 5.33; N, 31.77.

EXAMPLE 55

1-Dimethylaminosulfonyl-2-Amino-5(6)-(1,3,4-oxadiazol-2-yl)benzimidazole (A)

1-Dimethylaminosulfonyl-2-amino-5(6)-benzimidazolecarboxylic acid hydrazide.

Three grams of ethyl 1-dimethylaminosulfonyl-2-amino-5(6)-benzimidazolecarboxylate, 50 ml. of methanol and 6 ml. of hydrazine hydrate were refluxed for about 100 hours. The hydrazide product crystallized out of solution during the reaction. The hot reaction mixture was filtered to yield 200 mg. of 1-dimethylaminosulfonyl-2-amino-5-benzimidazolecarboxylic acid hydrazide, mp. about 229–230° C. (dec), confirmed by nuclear magnetic resonance spectrum.

Analysis: $C_{10}H_{14}N_6O_3S$ MW 298. Calcd: C, 40.30; H, 4.70; N, 28.20. Found: C, 40.21; H, 4.54; N, 28.33.

Upon cooling the filtrate yielded a solid which was collected. The solid was a mixture of isomeric acid hydrazides. The subsequent filtrates yielded two crops of crystals upon concentrating and cooling to give a combined yield of 350 mg. of 1-dimethylaminosulfonyl-2-amino-6-benzimidazole carboxylic acid hydrazide hydrate, mp. about 205°-206° C., confirmed by NMR.

Analysis: $C_{10}H_{14}N_6O_3S.H_2O$ MW 316. Calcd: C, 37.97; H, 5.06; N, 26.58. Found: C, 38.40; H, 4.41; N, 26.15.

(B)

1-Dimethylaminosulfonyl-2-(ethoxymethyleneamino-5(6)-(1,3,4-oxadiazol-2-yl)benzimidazole.

Three grams (0.01 mole) of 1-dimethylaminosulfonyl2-amino-5(6)-benzimidazolecarboxylic acid hydrazide and 100 ml. of ethyl orthoformate were heated at reflux for 24 hours with the use of a Dean-Stark trap. The reaction mixture was evaporated to dryness in vacuo. The residue was dissolved in ethyl acetate and the product was crystallized by concentrating and cooling to yield 580 mg. of 1-dimethylaminosulfonyl-2-(ethoxymethyleneamino)-5(6)-(1,3,4-oxadiazol2-yl)benzimidazole.

Analysis: $C_{14}H_{16}N_6O_4S$ MW 364. Calcd: C, 46.15; H, 4.40; N, 23.08. Found: C, 46.19; H, 4.38; N, 22.64.

(C)

1-Dimethylaminosulfonyl-2-amino-5(6)-(1,3,4oxadiazol-2-yl)benzimidazole.

Five hundred and eithty milligrams of 1-dimethylaminosulfonyl-2-(ethoxymethyleneamino)-5(6)-(1,3,4-oxadiazol2-yl)benzimidazole was stirred for 1 hour at room temperature in 10 ml. of 1N hydrochloric acid. The reaction mixture was filtered to yield 230 mg. of 1-dimethylaminosulfonyl-2-amino-5(6)-(1,3,4-oxadiazol-2-yl)benzimidazole hydrochloride, mp. 200° C. (dec)

Analysis: $C_{11}H_{12}N_6O_3S.HCl$ MW 344.5. Calcd: C, 38.32; H, 3.80; N, 24.38. Found: C, 38.54; H, 4.07; N, 24.61.

The acid filtrate from (C) above was treated with sodium carbonate until the solution was basic to litmus. A solid precipitated from the basic solution. The precipitated solid was filtered to yield 120 mg. of 1-dimethylaminosulfonyl-2-amino-5(6)-(1,3,4-oxadiazol-2-yl)benzimidazole, mp. 230-231° C. dec.

Analysis: $C_{11}H_{12}N_6O_3S$ MW 308. Calcd: C, 42.85; H, 4.19; N, 27.03. Found: C, 42.61; H, 3.92; N, 27.26.

EXAMPLE 56

1-Cyclohexylsulfonyl-2-amino-6-benzoylbenzimidazole

When the procedure of Example 29 was repeated using 475 g. of 2-amino-5(6)-benzoylbenzimidazole, 2.5 moles of sodium hydride, and 365 g. of cyclohexylsulfonyl chloride, there was obtained 120 g. of 1-cyclohexylsulfonyl-2-amino-6-benzoylbenzimidazole. mp. 210°–213° C. (dec)

Analysis: $C_{20}H_{21}N_3O_3S$ MW 383. Calcd: C, 62.64; H, 5.52; N, 10.96. Found: C, 62.43; H, 5.27; N, 10.51.

EXAMPLE 57

1-(Thien-2-ylsulfonyl)-2-amino-5(6)-benzoylbenzimidazole

When the procedure of Example 29 was repeated using 26.4 g. (1.1 mole) of sodium hydride, 260 g. (1.1 mole) of 2-amino-5(6)-benzoylbenzimidazole, and 200 g. of thiophenesulfonyl chloride, there was obtained 1-(thien-2-ylsulfonyl)-2-amino-5(6)-benzoylbenzimidazole. m/e 351.

EXAMPLE 58

1-Dimethylaminosulfonyl-2-amino-5(6)-hydroxybenzimidazole (A) 2-Amino-5(6)-methoxybenzimidazole Thirty three grams (0.24 mole) of 4-methoxy-o-phenylenediamine was stirred in 625 ml. of water. Twenty-five grams (0.24 mole) of cyanogen bromide in 30 ml. of methanol was added slowly to the aqueous reaction mixture. An additional 35 ml. of methanol was added. The reaction was continued at room temperature for about 17 hours. The reaction mixture was filtered and the filtrate was basified with a solution of 25 g. (0.25 mole) of potassium carbonate in 150 ml. of water. The mixture was allowed to stand until crystallization of the product was complete. The product was collected and recrystallized from 600 ml. of ethyl acetate to yield 10 g. of 2-amino-5(6)-methoxybenzimidazole.

(B) 2-Amino-5(6)-hydroxybenzimidazole

One and a half grams of 2-amino-5(6)-methoxybenzimidazole and 17 ml. of 48 percent hydrogen bromide were refluxed with stirring for one hour. The product crystallized upon refrigeration overnight. The product was collected to yield 0.40 g. of 2-amino-5(6)-hydroxybenzimidazole hydrobromide.

(C)

1-Dimethylaminosulfonyl-2-amino-5(6)-hydroxybenzimidazole

Twenty millimoles, 4.6 g., of 2-amino-5(6)-hydroxybenzimidazole, 20 ml. of acetone, 5.5 ml. (40 mmoles) of triethylamine, and 2.9 g. (20 mmoles) of dimethyl sulfamoyl chloride in 5 ml. of acetone were refluxed for about 20 hours. The reaction mixture was poured into 300 ml. of water. The aqueous mixture was extracted with ethyl acetate. The ethyl acetate extract was washed successively with water and saturated sodium chloride solution. After drying the ethyl acetate solution was evaporated in vacuo to give 3.0 g. of gummy residue. The residue was taken up in hot ethyl acetate and the product was allowed to crystallize. The product was collected to yield 523 mg. of the 6-isomer, 1-Dimethylaminosulfonyl-2-amino-6-hydroxybenzimidazole, mp. 217°–219° C. An analytical sample was prepared, mp. 227°–228° C.

Analysis $C_9H_{12}N_4O_3S$ MW 256 Calcd: C, 42.18; H, 4.72; N, 21.86; S, 12.51 Found: C, 42.35; H, 4.80; N, 21.80; S, 12.34.

The mother liquors form the crystallization of the 6-isomer were evaporated to yield 1.5 g. of solid residue. The material was chromatographed using 150 g. of Woelm silica gel packed with 1:1 toluene-ethyl acetate, the product was eluted with toluene-ethyl acetate, 300 ml. (1:1), 300 ml. (1:2) and 400 ml. (1:3) and ethyl acetate to end. Ten milliliter fractions were collected. Product started coming off at fraction 129. Fractions 214 to 228 were combined to provide 39 mg. of the 5-isomer, 1-dimethylaminosulfonyl-2-amino-5-hydroxybenzimidazole.

EXAMPLE 59

1-Dimethylaminosulfonyl-2-amino-5(6)-acetoxybenzimidazole

One millimole, 257 mg., of 1-dimethylaminosulfonyl-2-amino-5(6)-hydroxybenzimidazole was dissolved in 3 ml. of dimethylformamide (DMF). Sixty milligrams (1.1 mole) of sodium methylate were added to the reaction mixture. After about one minute, a solution of 107 mg. of acetic anhydride in 1 ml. of DMF was added. Within 5 minutes, 18 ml. of water and 17 ml. of pH 7.00 buffer were added to the reaction mixture. The product began to precipitate after a few minutes. After 30 minutes the product was collected to yield 170 mg. (57 percent) of 1-dimethylaminosulfonyl-2-amino-5(6)-acetoxybenzimidazole as an isomeric mixture.

Analysis: $C_{11}H_{14}N_4O_4S$ MW 298. Calcd: C, 44.29; H, 4.73; N, 18.78. Found: C, 44.13; H, 4.83; N, 18.72.

The following esters were prepared by the method of Example 59 using propionic, butyric or benzoic anhydride instead of acetic anhydride.

1-Dimethylaminosulfonyl-2-amino-5(6)-propionyloxybenzimidazole

Analysis $C_{12}H_{14}O_4S$ MW 310. Calcd: C, 46.14; H, 5.16; N, 17.94. Found: C, 45.87; H, 5.02; N, 17.76.

1-Dimethylaminosulfonyl-2-amino-5(6)-butyryloxybenzimidazole

Analysis $C_{13}H_{16}N_4O_4S$ MW 324. Calcd: C, 47.84; H, 5.56; N, 17.17. Found: C, 47.61; H, 5.33; N, 17.13.

1-Dimethylaminosulfonyl-2-amino-5(6)-benzoyloxybenzimidazole

Analysis $C_{16}H_{14}N_4O_4S$ MW 368. Calcd: C, 53.32; H, 4.48; N, 15.55. Found: C, 53.04; H, 4.41; N, 15.26.

EXAMPLE 60

1-Dimethylaminosulfonyl-2-acetamido-6-hydroxybenzimidazole

1-Dimethylaminosulfonyl-2-acetamido-6-acetoxybenzimidazole, 170 mg. (0.50 mmole), was dissolved in 3.0 ml. of dimethylformamide and 2.0 ml. of pH 10.0 buffer was added. One-half milliter of three percent hydrogen peroxide was added to the reaction mixture. The reaction mixture was allowed to stir at room temperature for about 10 minutes. The mixture was poured into 50 ml. of 0.1 N hydrochloric acid. The acid mixture was extracted with chloroform. The extract was washed successively with water and saturated sodium chloride solution. The chloroform solution was dried and evaporated in vacuo to yield 102 mg. of 1-dimethylaminosulfonyl-2-acetamido-6-hydroxybenzimidazole, mp. 175°–176° C., after crystallization Analysis $C_{11}H_{14}N_4O_4S$ MW 298 Calcd: C, 43.29; H, 4.73; N, 18.78; S, 10.75. Found: C, 44.24; H, 4.55; N, 18.51; S, 10.65.

EXAMPLE 61

1-Dimethylaminosulfonyl-2-acetamido-6-acetoxybenzimidazole

1-Dimethylaminosulfonyl-2-amino-6-hydroxybenzimidazole, 250 mg., 1 ml. of acetic anhydride and 0.10 mg. of sodium acetate (anhydrous) were warmed (hot water) for about ten minutes. Fifteen milliliters of water were added to the mixture with stirring. Product crystallized after one-half hour. The material was collected to yield 226 mg. (66 percent) of 1-dimethylaminosulfonyl-2-acetamido-6-acetoxybenzimidazole, mp. 164°–166° C. (ethyl acetate)

Analysis $C_{13}H_{16}N_4O_5S$ MW 340. Calcd: C, 45.88; H, 4.74; N, 16.46; S, 9.42. Found: C, 45.93; H, 4.70; N, 16.26; S, 9.62.

EXAMPLE 62

1-Isopropylsulfonyl-2-amino-5(6)-(n-propionyloxyiminobenzyl)benzimidazole

When 1 g. (0.003 mole) of 1-isopropylsulfonyl-2-amino-5-(6)-(α-hydroxyiminobenzyl)benzimidazole, 162 mg. (0.003 mole) of sodium methoxide, 10 ml. of dimethylformamide, and 0.3 ml. of propionic anhydride were substituted in the procedure of Example 42, there was obtained 860 mg. of 1-isopropylsulfonyl-2-amino-5(6)-(n-propionyloxyiminobenzyl)benzimidazole Analysis $C_{20}H_{22}N_4O_4S$ MW 414 Calcd: C, 57.96; H, 5.35; N, 13.52 Found: C, 58.20; H, ;b 5.36; N, 13.75

EXAMPLE 63

1-Isopropylsulfonyl-2-amino-5(6)-(n-butyryloxyiminobenzyl)benzimidazole

When 1 g. (0.003 mole) of 1-isopropylsulfonyl-2-amino-5(6)-(α-hydroxyiminobenzyl)benzimidazole, 162 mg. (0.003 mole) of sodium methoxide, 10 ml. of dimethylformamide, and 0.5 ml. of butyric anhydride were substituted in the procedure of Example 42, there was obtained 900 mg. of 1-isopropylsulfonyl-2-amino-5(6)-(n-butyryloxyiminobenzyl)benzimidazole.

Analysis $C_{21}H_{24}N_4O_4S$ MW 428. Calcd: C, 58.86; H, 5.65; N, 13.08. Found: C, 58.64; H, 5.44; N, 13.35.

EXAMPLE 64

1-Isopropylsulfonyl-2-amino-5(6)(n-pentanoyloxyiminobenzyl)benzimidazole

To a solution of 1 g. (0.003 mole) of 1-isopropylsulfonyl-2-amino-5(6)-(α-hydroxyiminobenzyl)benzimidazole in 10 ml. of dimethylformamide was added 162 mg. (0.003 mole) of sodium methoxide with stirring. The solution turned dark in color. Valeric anhydride, 0.6 ml. (0.003 mole, d=0.924), was added to the solution and the solution stirred for 2 hours. The solution was poured with stirring into 100 ml. of buffer (pH=7.00) and 100 ml. of water. The product was collected by filtration, washed with water, dried, dissolved in 10 ml. of chloroform, diluted with isopropyl ether on a steam bath to 50 ml., boiled to concentrate the volume, cooled to 0° C., and filtered to yield 700 mg., as an amorphous yellow foam, 1-isopropylsulfonyl-2-amino-5(6)-(n-pentanoyloxyiminobenzyl)benzimidazole.

Analysis $C_{22}H_{26}N_4O_4S$ MW 442 Calcd: C, 59.71; H, 5.92; N, 12.66 Found: C, 59.58; H, 6.16 N, 12.65

EXAMPLE 65

1-Isopropylsulfonyl-2-amino-5(6)-(pivaloyloxyiminobenzyl)benzimidazole

When 1 g. (0.003 mole) of 1-isopropylsulfonyl-2-amino-5(6)-(α-hydroxyiminobenzyl)benzimidazole, 0.43 ml. (0.003 ml.) of triethylamine, 10 ml. of chloroform, and 0.36 ml. of pivaloyl chloride were substituted in the procedure of Example 42, and followed by trituration with methanol/isopropyl ether, there was obtained 860 mg. of 1-isopropylsulfonyl-2-amino-5(6)-pivaloyloxyiminobenzyl)benzimidazole.

Analysis $C_{22}H_{26}N_4O_4S$ MW 442. Calcd: C, 59.71; H, 5.92; N, 12.66 Found: C, 59.47; H, 5.78; N, 12.44

EXAMPLE 66

1-Isopropylsulfonyl-2-amino-5(6)-(3-methoxycarbonylpropionyloxyiminobenzyl)benzimidazole To a solution of 1 g. (0.003 mole) of 1-isopropylsulfonyl-2-amino-5(6)-(α-hydroxyiminobenzyl)benzimidazole in 10 ml. of chloroform was added 0.43 ml. (0.003 mole) of triethylamine with stirring. To the solution was added 5 ml. of chloroform with 0.38 ml. (0.003 mole) of 3-carbomethoxypropionyl chloride with stirring. The solution stood overnight, was extracted twice with water, dried, filtered, concentrated under vacuum, taken up in benzene, and concentrated under vacuum to yield 950 mg. of 1-isopropylsulfonyl-2-amino-5(6)-(3-methoxycarbonylpropionyloxyiminobenzyl)benzimidazole.

Analysis $C_{22}H_{24}N_4O_6S$ MW 472 Calcd: C, 55.92; H, 5.12; N, 11.86 Found: C, 56.02; H, 5.09; N, 11.65

EXAMPLE 67

1-Isopropylsulfonyl-2-amino-5(6)-[2-(p-nitrobenzyloxycarbonyl)ethylcarbonyloxyiminobenzyl]benzimidazole When 1.8 g. (0.005 mole) of 1-isopropylsulfonyl-2-amino-(α-hydroxyiminobenzyl)benzimidazole in 20 ml. of chloroform, 0.8 ml. of triethylamine, and 1.2 g. of p-nitrobenzyloxycarbonylpropionyl chloride in 10 ml. of chloroform were substituted in the procedure of Example 66, there was obtained 2 g. of 1-isopropylsulfonyl-2-amino-5(6)-[2-(p-nitrobenzyloxycarbonyl)ethylcarbonyloxyiminobenzyl]benzimidazole Analysis $C_{28}H_{27}N_5O_8S$ MW 593. Calcd: C, 56.75; H, 4.42; N, 11.82. Found: C, 56.53; H, 4.69; N, 11.54.

EXAMPLE 68

1-Isopropylsulfonyl-2-amino-5(6)-(benzyloxycarbonylaminomethylcarbonyloxyiminobenzyl)benzimidazole One gram (0.005 mole) of benzyloxycarbonylaminomethylcarboxylic acid in 20 ml. of benzene was stirred and 0.9 ml. (0.01 mole) of oxalyl chloride and 1 drop of pyridine was added. The solution was stirred for 1 hour, warmed on a steam bath, concentrated under vacuum, taken up in benzene, concentrated under vacuum until dry. The residue was dissolved in 10 ml. of chloroform and added to 1.8 g. (0.005 mole) of 1-isopropylsulfonyl-2-amino-5(6)-(α-hydroxyiminobenzyl)benzimidazole and 0.8 ml. (0.005 mole) of triethylamine in 20 ml. chloroform. The solution stood at room temperature overnight. The solution was washed twice with water, buffer (pH=4), buffer (pH=10), dried, and concentrated to a residue. The residue was recrystallized from methanol, diluted with diisopropyl ether, and filtered to yield 840 mg. of 1-isopropylsulfonyl-2-amino-5(6)-(benzyloxycarbonylaminomethylcarbonyloxyiminobenzyl)benzimidazole, m/e 292 (loss of isopropylsulfonyl group and benzyloxycarbonylamino group).

EXAMPLE 69

1-Isopropylsulfonyl-2-amino-5(6)-(phthalimidomethylcarbonyloxyiminobenzyl)benzimidazole When 1 g. (0.005 mole) of phthalimidomethylcarboxylic acid, 0.9 ml. (1.3 g., 0.01 mole) of oxalyl chloride in 15 ml. of benzene, 1 drop of pyridine, 1.8 g. (0.005 mole) of 1-isopropylsulfonyl-2-amino-5(6)-(α-hydroxyiminobenzyl)benzimidazole, and 0.8 ml. (0.005 mole) of triethylamine were substituted in the procedure of Example 61, there was obtained 2.3 g. of 1-isopropylsulfonyl-2-amino-5(6)-(phthalimidomethylcarbonyloxyiminobenzyl)benzimidazole. m/e 545.

EXAMPLE 70

1-Isopropylsulfonyl-2-amino-5(6)-[2-(2-benzyloxycarbonyl-5-oxoisoxazolidin-4-yl)ethylcarbonyloxyiminobenzyl]benzimidazole When 0.9 g. (0.003 mole) of 3-(3-benzyloxycarbonyl-5-oxoisoxazolidin-4-yl)propionic acid in 20 ml. of benzene, 0.54 ml. (0.006 mole) of oxalyl chloride, 1 drop of pyridine, 1 g. (0.003 mole) of 1-isopropylsulfonyl-2-amino-5(6)-(α-hydroxyiminobenzyl)benzimidazole, and 0.43 ml. of triethylamine were substituted in the procedure of Example 68, there was obtained 1.7 g., as an amorphous foam, of 1-isopropylsulfonyl-2-amino-5(6)-[2-(2-benzyloxycarbonyl-5-oxoisoxazolidin-4-yl)ethylcarbonyloxyiminobenzyl]benzimidazole.

EXAMPLE 71

1-Dimethylaminosulfonyl-2-amino-6-(α-hydroxy-α-methylbenzyl)benzimidazole

To a solution of 600 ml. of tetrahydrofuran and 21.7 ml. (60 mmole) of methyl magnesium bromide in diethyl ether, under nitrogen, was added dropwise over 1 hour a solution of 4.1 g. (12 mmole) of 1-dimethylaminosulfonyl-2-amino-6-benzoylbenzimidazole in 180 ml. of tetrahydrofuran. The mixture was refluxed for 5 hours, poured into ice and 1N hydrochloric acid, extracted twice with diethyl ether, washed with saturated sodium chloride, dried, and filtered to yield 2.9 g., as an amorphous solid, of 1-dimethylaminosulfonyl-2-amino-6-(α-hydroxy-α-methylbenzyl)benzimidazole. m/e 360.

Analysis $C_{17}H_{20}N_4O_3S$ MW 360 Calcd: C, 56.67; H, 5.59; N, 15.54 Found: C, 56.77; H, 5.46; N, 15.27

EXAMPLE 72

1-Dimethylaminosulfonyl-2-amino-6-(α-methylenebenzyl)benzimidazole

Two grams (5.5 mmole) of 1-dimethylaminosulfonyl-2-amino-6-(α-hydroxy-α-methylbenzyl)benzimidazole in 130 ml. of chloroform was reacted with 1.3 g. of p-toluenesulfonic acid. The solution was refluxed with stirring for 6 hours. The solution was then washed with saturated sodium carbonate, dried, and filtered to yield 1.7 g. of 1-dimethylaminosulfonyl-2-amino-6-(α-methylenebenzyl)benzimidazole, m.p. 201°–202° C.

Analysis $C_{17}H_{18}N_4O_2S$ MW 342 Calcd: C, 59.63; H, 5.30; N, 16.36 Found: C, 59.67; H, 5.35; N, 16.07

EXAMPLE 73

1-Dimethylaminosulfonyl-2-amino-6-(α-ethyl-α-hydroxybenzyl)benzimidazole

When the procedure of Example 71 was repeated using 100 ml. tetrahydrofuran, 22.2 ml. (60 mmole) of ethyl magnesium bromide (2.7 mmole/ml) in diethyl ether, and 4.1 g. of 1-dimethylaminosulfonyl-2-amino-6-benzoylbenzimidazole, there was obtained 3.2 g., as a foam, of 1-dimethylaminosulfonyl-2-amino-6-(α-ethyl-α-hydroxybenzyl)benzimidazole.

High resolution mass spec. for $C_{18}H_{22}N_4O_3S$ Calcd: 374.14123 Found: 374.141

EXAMPLE 74

1-Dimethylaminosulfonyl-2-amino-6-(α-ethylidenebenzyl)benzimidazole

When the procedure of Example 72 was repeated using 1.2 g. (3.21 mmole) of 1-dimethylaminosulfonyl-2-amino-6-(α-ethyl-α-hydroxybenzyl)benzimidazole, 750 mg. of p-toluenesulfonic acid, and 100 ml. of chloroform, there was obtained 388 mg. of 1-dimethylaminosulfonyl-2-amino-6-(α-ethylidenebenzyl)benzimidazole, m.p. 200°–202° C. (dec.)

High resolution mass spec. for $C_{18}H_{20}N_4O_2S$ Calcd: 356.13107 Found: 356.131

EXAMPLE 75

70.7 Grams of 1-Dimethylaminosulfonyl-2-amino-6-(α-acetoxyiminobenzyl)benzimidazole was dissolved in a mixture of 200 ml. ethanol and 150 ml. chloroform. The solution was concentrated by boiling to 300 ml. and allowed to stand at room temperature overnight. The crystals which formed were filtered to yield 6.2 g. of 1-dimethylaminosulfonyl-2-amino-6-(syn-α-acetoxyiminobenzyl)benzimidazole, m.p. 175°–179° C.

The filtrate from the above paragraph was condensed to 100 ml. and cooled. The crystals which formed were 8.25 g. of 1-dimethylaminosulfonyl-2-amino-6-(anti-α-acetoxyiminobenzyl)benzimidazole, m.p. 190°–195° C.

EXAMPLE 76

When 1 g. of 1-isopropylsulfonyl-2-amino-6-(α-hydroxyiminobenzyl)benzimidazole in 4 ml. of dimethylsulfoxide was subjected to high pressure chromatography using 50:50 methanol:water in a reverse phase 2.5 × 50 cm. column (LP-1/$C_{18}$ silica gel which is a chemically modified silica gel known in the art) with a pressure of 70–2000 psi., there was obtained 70 mg. of 1-isopropylsulfonyl-2-amino-6-(anti-α-hydroxyiminobenzyl)benzimidazole and 30 mg. of 1-isopropylsulfonyl-2-amino-6-(syn-α-hydroxyiminobenzyl)benzimidazole.

EXAMPLE 77

1-Dimethylaminosulfonyl-2-amino-6-(α-isopropyl-α-hydroxybenzyl)benzimidazole

When the procedure of Example 71 was repeated using 4.1 g. (12 mmole) of 1-dimethylaminosulfonyl-2-amino-6-benzoylbenzimidazole in 180 ml. of tetrahydrofuran, 100 ml. tetrahydrofuran, and 28.6 ml. (60 mmole) of isopropyl magnesium chloride in 100 ml. of tetrahydrofuran, there was obtained 1-dimethylaminosulfonyl-2-amino-6-(α-isopropyl-α-hydroxybenzyl)benzimidazole, yield 65%.

EXAMPLE 78

1-Dimethylaminosulfonyl-2-amino-6-(α-isopropylidenebenzyl)benzimidazole

When the procedure of Example 72 was repeated using 1.2 g. (3.2 mmoles) of 1-dimethylaminosulfonyl-2-amino-6-(α-isopropyl-α-hydroxybenzyl)benzimidazole, 750 mg. of p-toluenesulfonic acid, and 100 ml. of chloroform, there was obtained 1-dimethylaminosulfonyl-2-amino-6-(α-isopropylidenebenzyl)benzimidazole.

We claim:

1. A compound of the formula

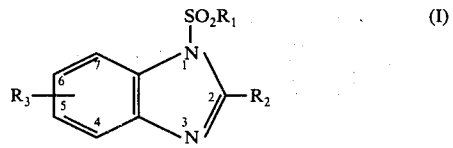

wherein $R_1$ is $C_1$–$C_5$ alkyl, $C_3$–$C_7$ cycloalkyl, phenyl, furyl, thienyl, or $R_4R_5N$-, wherein $R_4$ and $R_5$ are independently $C_1$–$C_3$ alkyl or $R_4$ and $R_5$, when taken together with the nitrogen atom to which they are attached, are pyrrolidino, piperidino, or morpholino;

$R_2$ is amino, formamido, acetamido, propionamido or butyramido;

$R_3$ is $C_2$–$C_8$ alkanoyloxy, phenylacetoxy, or benzoyloxy;

wherein $R_6$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, benzyl, phenyl or phenyl substituted by $C_1$–$C_4$ alkyl, $C_1$–$C_4$ alkoxy, chloro, bromo, iodo, nitro or trifluoromethyl; or Z=C($R_6$)-, wherein Z is hydroxyimino, $C_1$–$C_4$ alkoxyimino, $C_1$–$C_4$ acyloxyimino, benzyloxyimino, benzoyloxyimino, hydrazono, thiocarbamylhydrazono, carboxymethoxyimino, methoxycarbonylhydrazono, ethoxycarbonylhydrazono, carbamylhydrazono, $C_1$–$C_4$ alkoxycarbonylethylcarbonyloxyimino, benzyloxycarbonylaminomethylcarbonyloxyimino, p-nitrobenzyloxycarbonylethylcarbonyloxyimino, or phthalimidomethylcarbonyloxyimino; and $R_3$ is at the 5 or 6 position.

2. The compound of claim 1 which is 1-dimethylaminosulfonyl-2-amino-6-benzoylbenzimidazole.

3. The compound of claim 1 which is 1-isopropylsulfonyl-2-amino-6-benzoylbenzimidazole.

4. The compound of claim 1 which is 1-dimethylaminosulfonyl-2-amino-5(6)-butyrylbenzimidazole.

5. A compound of claim 1 wherein $R_3$ is Z=C($R_6$)-, wherein $R_6$ is phenyl or phenyl substituted by chloro and Z is hydroxyimino.

6. The compound of claim 5 which is 1-isopropylsulfonyl-2-amino-5(6-(α-hydroxyiminobenzyl)benzimidazole.

7. The compound of claim 5 which is 1-dimethylaminosulfonyl-2-amino-5(6)-(α-hydroxyiminobenzyl)benzimidazole.

8. The compound of claim 5 which is 1-dimethylaminosulfonyl-2-amino-5(6)-(α-hyroxyimino-p-chlorobenzyl)benzimidazole.

9. A compound of claim 1 wherein $R_3$ is $Z=C(R_6)-$, wherein $R_6$ is phenyl and Z is $C_1-C_4$ alkoxyimino.

10. The compound of claim 9 which is 1-dimethylaminosulfonyl-2-amino-5(6)-(α-ethoxyiminobenzyl)benzimidazole.

11. The compound of claim 9 which is 1-dimethylaminosulfonyl-2-amino-5(6)-(α-propoxyiminobenzyl)benzimidazole.

12. The compound of claim 9 which is 1-dimethylaminosulfonyl-2-amino-5(6)-(α-methoxyiminobenzyl)benzimidazole.

13. The compound of claim 9 which is 1-isopropylsulfonyl-2-amino-5(6)-(α-methoxyiminobenzyl)benzimidazole.

14. A compound of claim 1 wherein $R_3$ is $Z=C(R_6)-$, wherein $R_6$ is phenyl and Z is $C_1-C_4$ acyloxyimino.

15. The compound of claim 14 which is 1-dimethylaminosulfonyl-2-amino-5(6)-(α-acetoxyiminobenzyl)benzimidazole.

16. The compound of claim 14 which is 1-dimethylaminosulfonyl-2-amino-5(6)-(α-propionyloxyiminobenzyl)benzimidazole.

17. The compound of claim 14 which is 1-isopropylsulfonyl-2-amino-5(6)-(α-acetoxyiminobenzyl)benzimidazole.

18. The compound of claim 14 which is 1-dimethylaminosulfonyl-2-acetamido-5(6)-(α-acetoxyiminobenzyl)benzimidazole.

19. A compound of claim 1 wherein $R_3$ is $Z=C(R_6)-$, wherein $R_6$ is phenyl or $C_1-C_7$ alkyl and Z is benzoyloxyimino, or thiocarbamylhydrazono.

20. The compound of claim 19 which is 1-dimethylaminosulfonyl-2-amino-5(6)-(α-benzoyloxyiminobenzyl)benzimidazole.

21. The compound of claim 19 which is 1-dimethylaminosulfonyl-2-amino-5(6)-thiocarbamylhydrazonomethyl-benzimidazole.

22. The compound of claim 1 which is 1-cyclohexylsulfonyl-2-amino-6-benzoyolbenzimidazole.

23. The compound of claim 1 which is 1-dimethylaminosulfonyl-2-amino-6-(α-acetoxyiminobenzyl)benzimidazole.

24. The compound of claim 1 which is 1-dimethylaminosulfonyl-2-amino-6-(syn-α-acetoxyiminobenzyl)benzimidazole.

25. The compound of claim 1 which is 1-dimethylaminosulfonyl-2-amino-6-(anti-α-acetoxyiminobenzyl)benzimidazole.

26. The compound of claim 1 which is 1-isopropylsulfonyl-2-amino-6-(α-hydroxyiminobenzyl)benzimidazole.

27. The compound of claim 1 which is 1-isopropylsulfonyl-2-amino-6-(anti-α-hydroxyiminobenzyl)benzimidazole.

28. The compound of claim 1 which is 1-isopropylsulfonyl-2-amino-6-(syn-α-hydroxyiminobenzyl)benzimidazole.

29. The compound of claim 1 which is b 1-isopropylsulfonyl-2-amino-5(6)-(n-propionyloxyiminobenzyl)benzimidazole.

30. The compound of claim 1 which is 1-dimethylaminosulfonyl-2-amino-5(6)-(α-butyryloxyiminobenzyl)benzinidazole.

31. The compound of claim 1 which is 1-isopropylsulfonyl-2-amino-5(6)-(n-butyryloxyiminobenzyl(benzimidazole.

32. The compound of claim 1 which is 1-isopropylsulfonyl-2-amino-5(6)-(3-methoxycarbonylpropionyloxyiminobenzyl)benzimidazole.

33. The compound of claim 1 which is 1-isopropylsulfonyl-2-amino-5(6)-[2-(p-nitrobenzyloxycarbonyl)ethylcarbonyloxyiminobenzyl]benzimidazole.

34. The compound of claim 1 which is 1-isopropylsulfonyl-2-amino-5(6)-(benzyloxycarbonylaminomethylcarbonyloxyiminobenzyl)benzimidazole.

35. The compond of claim 1 which is 1-isopropylsulfonyl-2-amino-5(6)-(phthalimidomethylcarbonyloxyiminobenzyl)benzimidazole.

36. 1-Dimethylaminosulfonyl-2-amino-5(6)-(α-methoxycarbonyloxyiminobenzyl)benzimidazole.

37. 1-Dimethylaminosulfonyl-2-amino-5(6)-(n-pentanoyloxyiminobenzyl)benzimidazole.

38. 1-Isopropylsulfonyl-2-amino-5(6)-(n-pentanoyloxyiminobenzyl)benzimidazole.

39. 1-Dimethylaminosulfonyl-2-amino-5(6)-(pivaloyloxyiminobenzyl)benzimidazole.

40. 1-Isopropylsulfonyl-2-amino-5(6)-(pivaloyloxyiminobenzyl)benzimidazole.

* * * * *